US007179646B2

(12) United States Patent
Young et al.

(10) Patent No.: US 7,179,646 B2
(45) Date of Patent: *Feb. 20, 2007

(54) GENE EXPRESSION USING T CELL FACTOR RESPONSIVE ELEMENT

(75) Inventors: Lawrence S. Young, West Midlands (GB); Kai S. Lipinski, Staffordshire (GB); Christopher J. Wrighton, Cheshire (GB)

(73) Assignee: Innovata PLC, London (GB)

( * ) Notice: Subject to any disclaimer, the term of this patent is extended or adjusted under 35 U.S.C. 154(b) by 83 days.

This patent is subject to a terminal disclaimer.

(21) Appl. No.: 10/607,479

(22) Filed: Jun. 26, 2003

(65) Prior Publication Data

US 2004/0048293 A1    Mar. 11, 2004

Related U.S. Application Data

(63) Continuation of application No. 09/798,128, filed on Mar. 2, 2001, now Pat. No. 6,608,037.

(60) Provisional application No. 60/187,465, filed on Mar. 6, 2000.

(30) Foreign Application Priority Data

Mar. 2, 2000    (GB) ................................. 0005099.7
Mar. 1, 2001    (WO) ..................... PCT/GB01/00856

(51) Int. Cl.
    *C12N 15/85*    (2006.01)
    *C12N 15/63*    (2006.01)
    *A61K 48/00*    (2006.01)
(52) U.S. Cl. ................... 435/320.1; 435/325; 435/455; 435/456; 424/93.2; 514/44
(58) Field of Classification Search ..................... None
    See application file for complete search history.

(56) References Cited

U.S. PATENT DOCUMENTS 5,166,320 A      11/1992    Wu et al.
6,608,037 B2 *   8/2003     Young et al. .................. 514/44

FOREIGN PATENT DOCUMENTS

| EP | 0 939 122 A1 | 9/1999 |
|---|---|---|
| WO | WO 91/17773 | 11/1991 |
| WO | WO 91/18088 | 11/1991 |
| WO | WO 93/08288 | 4/1993 |
| WO | WO 93/18759 | 9/1993 |
| WO | WO 95/02698 | 1/1995 |
| WO | WO 95/30020 | 11/1995 |
| WO | WO 96/41606 | 12/1996 |
| WO | WO 98/07876 | 2/1998 |
| WO | WO 98/35984 | 8/1998 |
| WO | WO 98/41631 | 9/1998 |
| WO | WO 00/56909 | 9/2000 |

OTHER PUBLICATIONS

Anderson, W.F., "Human gene therapy," *Nature*, 392 (*Supp*):25-30, Apr. 30, 1998.
Calos, M., "The potential of extrachromosomal replicating vectors for gene therapy," *TIG*, 12(11):463-466, 1996.
Chowdhury, J.R. et al., "Long-Term Improvement of Hypercholesterolemia After *ex Vivo* Gene Therapy in LDLR-Deficient Rabbits," *Science*, 254:1802-1805, Dec. 20, 1991.
Cotton, M. et al., "Receptor-Mediated Transport of DNA into Eukaryotic Cells," *Meth. Enzymol.*, 217:618-644, 1992.
Eastman, Q. and Grosschedl, R., "Regulation of LEF-1/TCF transcription factors by Wnt and other signals," *Current Opin. Cell Biol.*, 11:233-240, 1999.
Emerson, S.G., "*Ex Vivo* Expansion of Hematopoietic Precursors, Progenitors, and Stem Cells: The Next Generation of Cellular Therapeutics," *Blood*, 87(8):3082-3088, Apr. 15, 1996.
Fallaux, F.J. et al., "New Helper Cells and Matched Early Region 1-Deleted Andenovirus Vectors Prevent Generation of Replication-Competent Adenoviruses," *Human Gene Ther.*, 9:1909-1917, Sep. 1, 1998.
Flotte, T.R. et al., "Stable *in vivo* expression of the cystic fibrosis transmembrane conductance regulator with an adeno-associated virus vector," *Proc. Natl. Acad. Sci. USA*, 90:10613-10617, Nov. 1993.
He, T.C. et al., "Identification of c-*MYC* as a Target of the APC Pathway," *Science*, 281:1509-1512, Sep. 4, 1998.
Hengge, U.R. et al., "Cytokine gene expression in epidermis with biological effects following injection of naked DNA," *Nature Genetics*, 10:161-166, 1995.
Hickman, M.A. et al., "Gene Expression Following Direction Injection of DNA into Liver," *Human Gene Ther.*, 5:1477-1483, Dec. 1994.
Hitt, M.M. et al., "Human Adenovirus Vectors for Gene Transfer into Mammalian Cells," *Advances in Pharmacology*, 40:137-206, 1997.
Keown, W.A. et al., "Methods for Introducing DNA into Mammalian Cells," *Methods Enzymol.*, 185:527-537, 1990.
Korinek, V. et al., "Constitutive Transcriptional Activation by a β-catenin-Tcf Complex in APC $^+$ Colon Carcinoma," *Science*, 275:1784-1787, Mar. 21, 1997.

(Continued)

*Primary Examiner*—Scott D. Priebe
(74) *Attorney, Agent, or Firm*—Cozen O'Connor, P.C.

(57) ABSTRACT

Disclosed are DNA elements and constructs useful for obtaining tumor-selective gene expression in tumors having a mutated β-catenin/APC pathway. In particular, the use of these constructs to express genes encoding therapeutic proteins in colorectal cancer cells is described. The constructs comprise multiple repeats of a TCF-binding element operably linked to a promoter. By means of such a construct, tumor cell-specific expression of a prodrug-converting enzyme such as nitroreductase may be achieved. Coupled with systemic administration of a suitable prodrug, such as CB1954, selective killing of such tumor cells can be demonstrated.

22 Claims, 23 Drawing Sheets

OTHER PUBLICATIONS

Figure 2A:
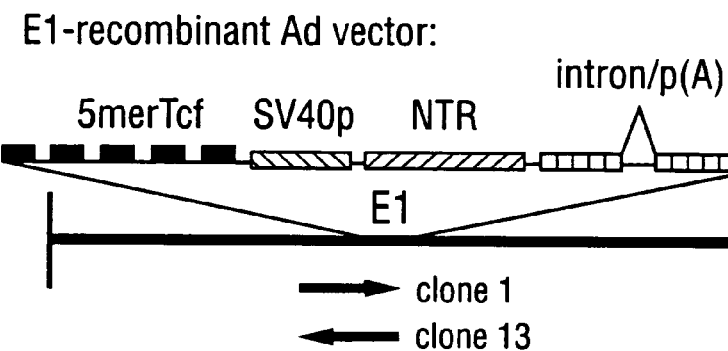

Kucherlapati, R. and Skoultchi, A.I., "Introduction of Purified Genes into Mammalian Cells," *Crit. Rev. Biochem.*, 16(4):349-379, 1984.

Lickert, H. et al., "Wnt/β-catenin signaling regulates the expression of the homeobox gene *Cdx1* in embryonic intestine," *Development*, 127:3805-3813, 2000.

Love, J.J. et al., "Structural basis for DNA bending by the architectural transcription factor LEF-1," *Nature*, 376:791-795, Aug. 31, 1995.

Mack, K.D. et al., "Cationic Lipid Enhances In Vitro Receptor-Mediated Transfection," *The American Journal of the Medical Sciences*, 307(2):138-143, 1994.

Meyer, K.B. et al., "Intratracheal gene delivery to the mouse airway: characterization of plasmid DNA expression and pharmacokinetics," *Gene Therapy*, 2:450-460, 1995.

Morin, P.J. et al., "Activation of β-Catenin-Tcf Signaling in Colon Cancer by Mutations in β-Catenin or APC," *Science*, 275:1787-1790, Mar. 21, 1997.

Miller, J.L. et al., "Recombinant adeno-associated virus (rAAV)—mediated expression of a human γ-globin gene in human progenitor-derived erythroid cells," *Proc. Natl. Acad. Sci. USA*, 91:10183-10187, Oct. 1994.

Philip, R. et al., "Efficient and Sustained Gene Expression in Primary T Lymphocytes and Primary and Cultured Tumor Cells Mediated by Adeno-Associated Virus Plasmid DNA Complexed to Cationic Liposomes," *Mol. Cell. Biol.*, 14(4):2411-2418, Apr. 1994.

Plank, C. et al., "The Influenced of Endosome-disruptive Peptides on Gene Transfer Using Synthetic Virus-like Gene Transfer Systems," *J. Biol. Chem.*, 269(17):12918-12924, Apr. 29, 1994.

Russell, D.W. et al., "Adeno-associated virus vectors preferentially transduced cells in S phase," *Proc. Natl. Acad. Sci. USA*, 91:8915-8919, Sep. 1994.

Shtutman, M. et al., "The cyclin D1 gene is a target of the β-catenin/LEF-1 pathway," *Proc. Natl. Acad. Sci. USA*, 96:5522-5527, May 1999.

Sikes, M.L. et al., "*In Vivo* Transfer into Rabbit Thyroid Follicular Cells by Direct DNA Injection," *Human Gene Ther.*, 5:837-844, 1994.

Tetsu, O. and McCormick, F., "β-Catenin regulates expression of cyclin D1 in colon carcinoma cells," *Nature*, 398:422-426, Apr. 1, 1999.

Trubetskoy, V.S. et al., "Use of N-Terminal Modified Poly(L-lysine)-Antibody Conjugate as a Carrier for Targeted Gene Delivery in Mouse Lung Endothelial Cells," *Bioconjugate Chem.*, 3:323-327, 1992.

Ustav, M. and Stenlund, A., "Transient replication of BPV-1 requires two viral polypeptides encoded by the E1 and E2 open reading frames," *The EMBO J.*, 10(2):449-457, 1991.

van de Wetering, M. et al., "Identification and cloning of TCF-1, a T lymphocyte-specific transcription factor containing a sequence-specific HMG box," *The EMBO J.*, 10(1):123-132, 1991.

Vile, R.G. and Hart, I.R., "*In Vitro* and *in Vivo* Targeting of Gene Expression to Melanoma Cells," *Cancer Res.*, 53:962-967, 1993.

Walsh, C.E. et al., "Regulated high level expression of a human γ-globin gene introduced into erythroid cells by an adeno-associated virus vector," *Proc. Natl. Acad. Sci. USA*, 89:7257-7261, Aug. 1992.

Watanabe, M. et al., "Nucleotide sequence of *Salmonella typhimurium* nitroreductase gene," *Nucleic Acids Res.*, 18(4):1059, 1990.

Wilson, J.M. et al., "*Ex Vivo* Gene Therapy of Familial Hypercholesterolemia," *Human Gene Ther.*, 3:179-222, 1992.

Wilson, J.M. et al., "Hepatocyte-directed Gene Transfer *in vivo* Leads to Transient Improvement of Hypercholesterolemia in Low Density Lipoprotein Receptor-deficient Rabbits," *J. Biol. Chem.*, 267(2):963-967, Jan. 15, 1992.

Wolff, J.A. et al., "Direct Gene Transfer into Mouse Muscle in Vivo," *Science*, 247:1465-1468, Mar. 23, 1990.

Wu and Wu, "Receptor-mediated Gene Delivery and Expression *in Vivo*," *J. Biol. Chem.*, 263(29):14621-14624, Oct. 15, 1988.

Besnard-Guerin, C. et al., HIV-1 Vpu Sequesters β-Transducin Repeat-containing Protein (βTrCP) in the Cytoplasm and Provokes the Accumulation of β-Catenin and Other $SCF^{\beta TrCP}$ Substrates, *J. Biological Chemistry*, 279(1):788-795, Jan. 2, 2004.

Cheon, S.S. et al., "β-Catenin stabilization dysregulates mesenchymal cell proliferation, motility, and invasiveness and causes aggressive fibromatosis and hyperplastic cutaneous wounds," *PNAS*, 99(10):6973-6978, May 14, 2002.

Chilosi, M. et al., Aberrant Wnt/β-Catenin Pathway Activation in Idiopathic Pulmonary Fibrosis, *American Journal of Pathology*, 162(5):1495-1502, May 2003.

Mak, B.C. et al., The Tuberin-Hamartin Complex Negatively Regulates β-Catenin Signaling Activity, *J. Biological Chemistry*, 278(8):5947-5951, 2003.

Moon, R.T. et al., "WNT and β-Catenin Signalling: Diseases and Therapies," *Nature Reviews, Genetics*, 5:689-699, Sep. 2004.

\* cited by examiner

FIG.1a
5merTcf-SV40-Luc reporter construct (CTL501):
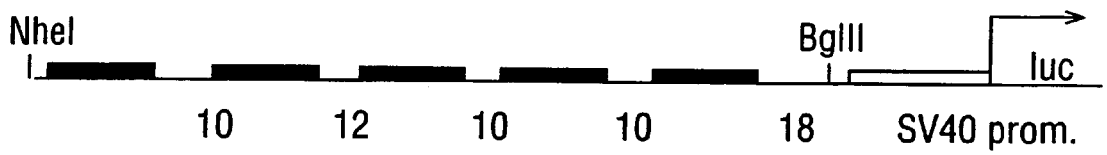
FIG. 1b
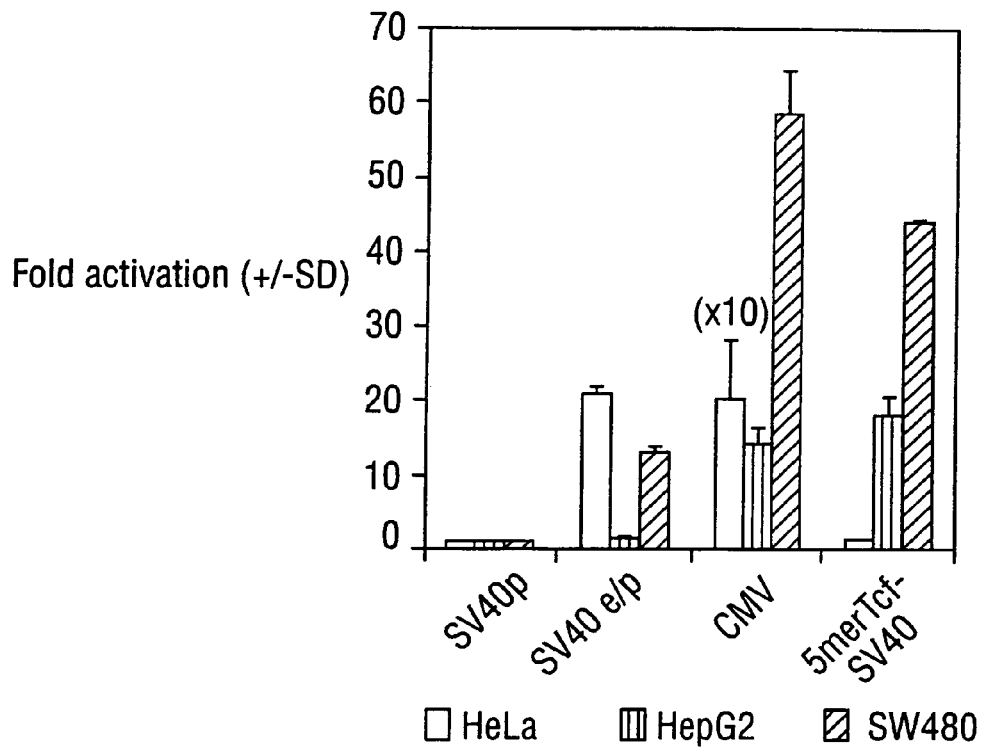
☐ HeLa  ☒ HepG2  ▨ SW480
FIG. 1c
5merTcf-SV40 (CTL501) antisense strand
TTGAGATGCAGATCGCAGATCT<u>GATAAAGG</u>TGCATTTAGA<u>*GATCAAAG*</u>
<u>*G*</u>TAGGACTCTT<u>*GATCAAAGG*</u>ACTGAATTCCTT<u>*GATCAAAGG*</u>TGCATTTAG
A<u>*GATCAAAGG*</u>TAGGACTCTTT<u>*GATCAAAGG*</u>GACTAGTAAGCTTGCTAGC
ACGCGTAAGAGCTCGGTACC

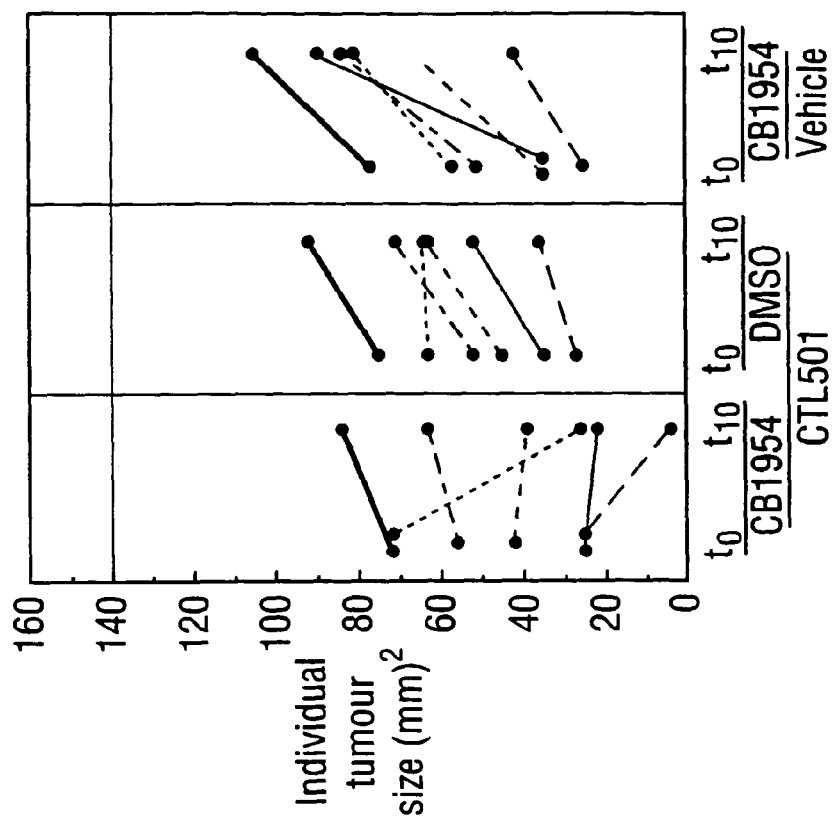
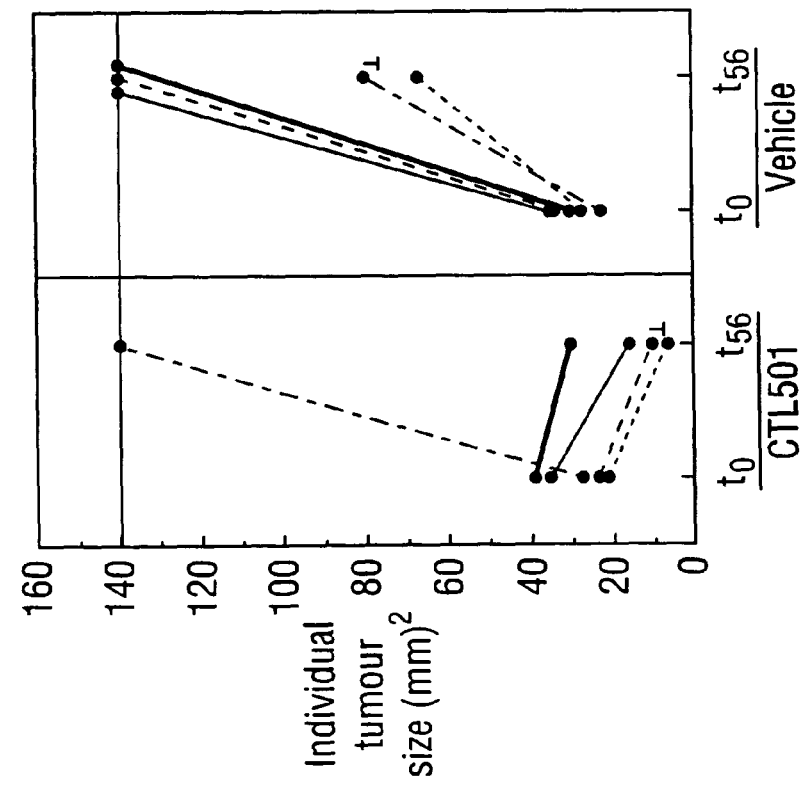
FIG. 3b
FIG. 3a

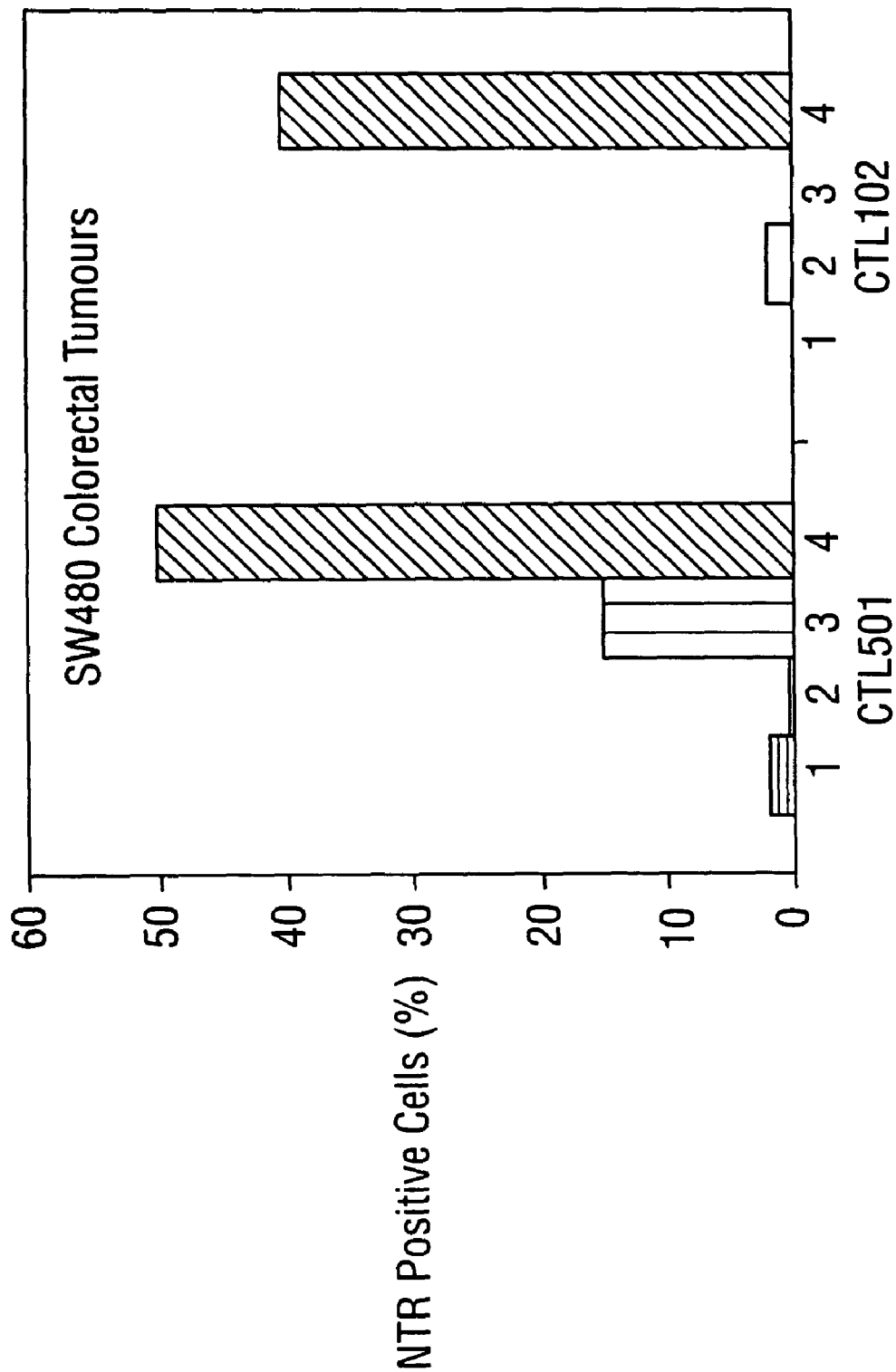

FIG. 6a
5merTcf-E1BTATA-Luc reporter construct (CTL502):
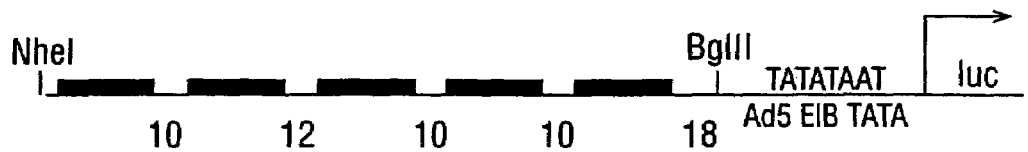
FIG. 6b
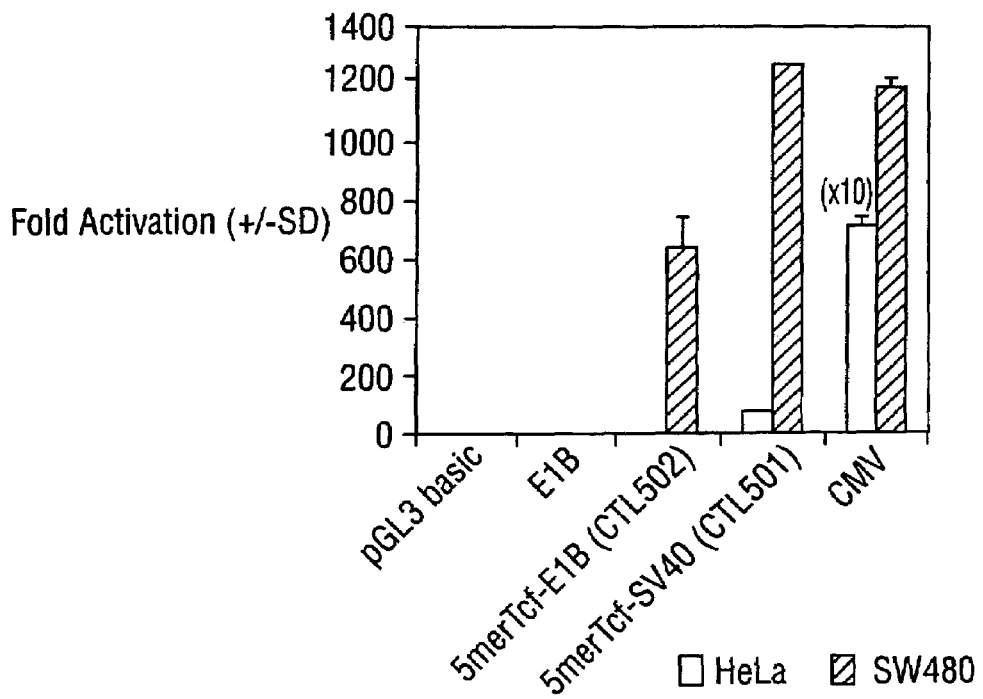
FIG. 6c
E1BTATA clone 2 antisense strand
GGATGCCAAGCTTTTTAGCTTCCTTAGCTCCTGAAAATCTCGCCAAGCTGA
TGAATTCGAGCTGGCGC*ATTATATA*CCCTCTAGAGTCGACGGATCGAGATC
TCGAGCCCGGGCTAGCACGCGTAAGAGCTCGGTACC

FIG. 9c (i)

2merTcf-E1BTATA clone 9 antisense strand

ATCGAGATCTGATAAAGGTGCATTTAGA<u>*GATCAAAGG*</u>TAGGTTACTCTTTG

AATTCAGGTGCAATTTAAAGGTAGGAAACTCTT<u>*GATCAAAGG*</u>ACTAGTAAG

CTTGCTAGCACGCGTAAGAGCTCGGTACC

3merTcf-E1BTATA clone 2 antisense strand

ATCGAGATCTGATAAAGGTGCATTTAGA<u>*GATCAAAGG*</u>TAGGTTACT

CTT<u>*GATCAAAGG*</u>ACTGAATTCAGGAAACTCTT<u>*GATCAAAGG*</u>ACTAGTAAGCT

TGCTAGCACGCGTAAGAGCTCGGTACC

3merTcf-E1BTATA clone 13 antisense strand

ATCGAGATCTGATAAAGGTGCATTTAGA<u>*GATCAAAGG*</u>TAGTCACAGGTGC

AATTTAGA<u>*GATCAAAGG*</u>TAGGAATT<u>*GATCAAAGG*</u>ATAGTAAGCTTGCTAGC

ACGCGTAAGAGCTCGGTACC

4merTcf-E1BTATA clone 15 antisense strand

ATCGAGATCTGATAAAGGTTCTT<u>*GATCAAAGG*</u>ACTGAATTCCTT<u>*GATCAAA*</u>

<u>*GG*</u>TGCAATTTAGA<u>*GATCAAAGG*</u>TAGGAAACTCTT<u>*GATCAAAGG*</u>ACTAGTAA

GCTTGCTAGCACGCGTAAGAGCTCGGTACC

FIG. 9c (ii)

4merTcf-E1BTATA clone 34 antisense strand

ATCGAGATCGATAAAGGTGCATTTAGAC*GATCAAAGG*TAGGTTACTCTT*GA*

*TCAAAGG*AATTCCTT*GATCAAAGG*TGCAATTTAGAGAAGGTAGGAAACTCT

T*GATCAAAGG*ACTAGTAAGCTTGCTAGCACGCGTAAGAGCTCGGTACC

FIG.10a

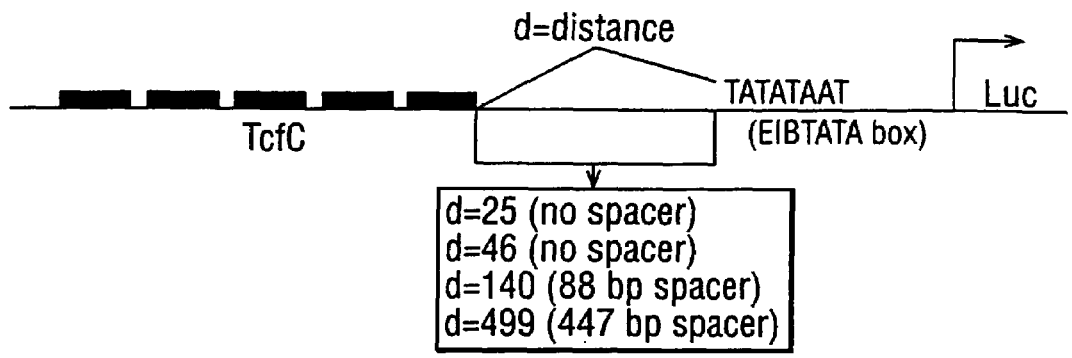

d=25 (no spacer)
d=46 (no spacer)
d=140 (88 bp spacer)
d=499 (447 bp spacer)

FIG.10b

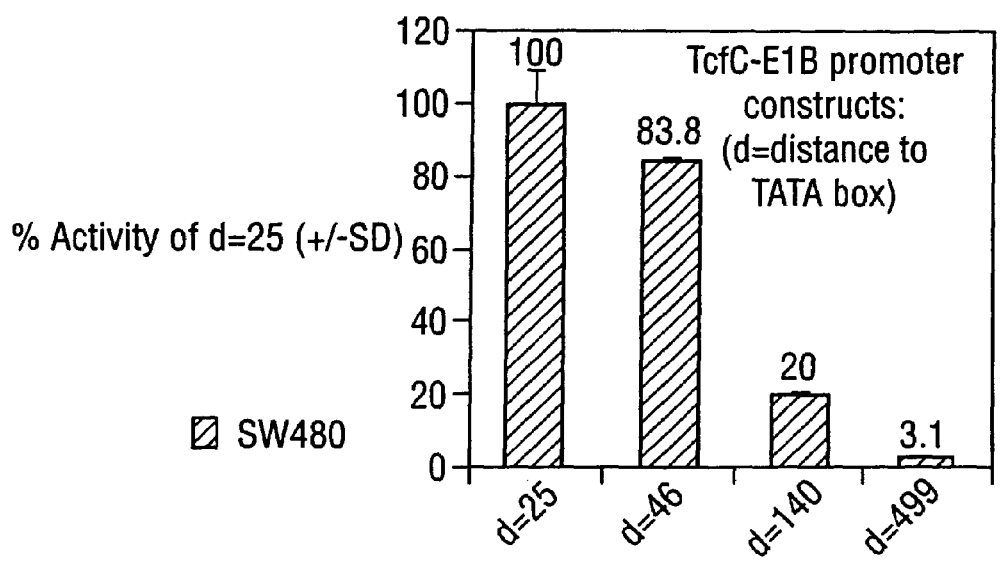

FIG.10c

/TcfC-EIBTATA (d=25) clone 6 antisense strand

TACCAACAGTACCGGAATGCCAAGCTAGCTTTTTAGCTTCCTTAGCTCCTG

AAAATCTCGCCAAGCTGATGAATTCGAGCTGGCGCATTATATACCCTCTG

ATAAAGGTGCATTTAGA*GATCAAAGG*TAT*GATCAAAGG*ACTT*GATCAAAGG*T

GA*GATCAAAGG*TATT*GATCAAAGG*ACTAGAGCTTACTTAGATCGCAGATCTC

GAGCCCGGGCTAGCACGCGTAAGAGCTCGGTACCTATCG

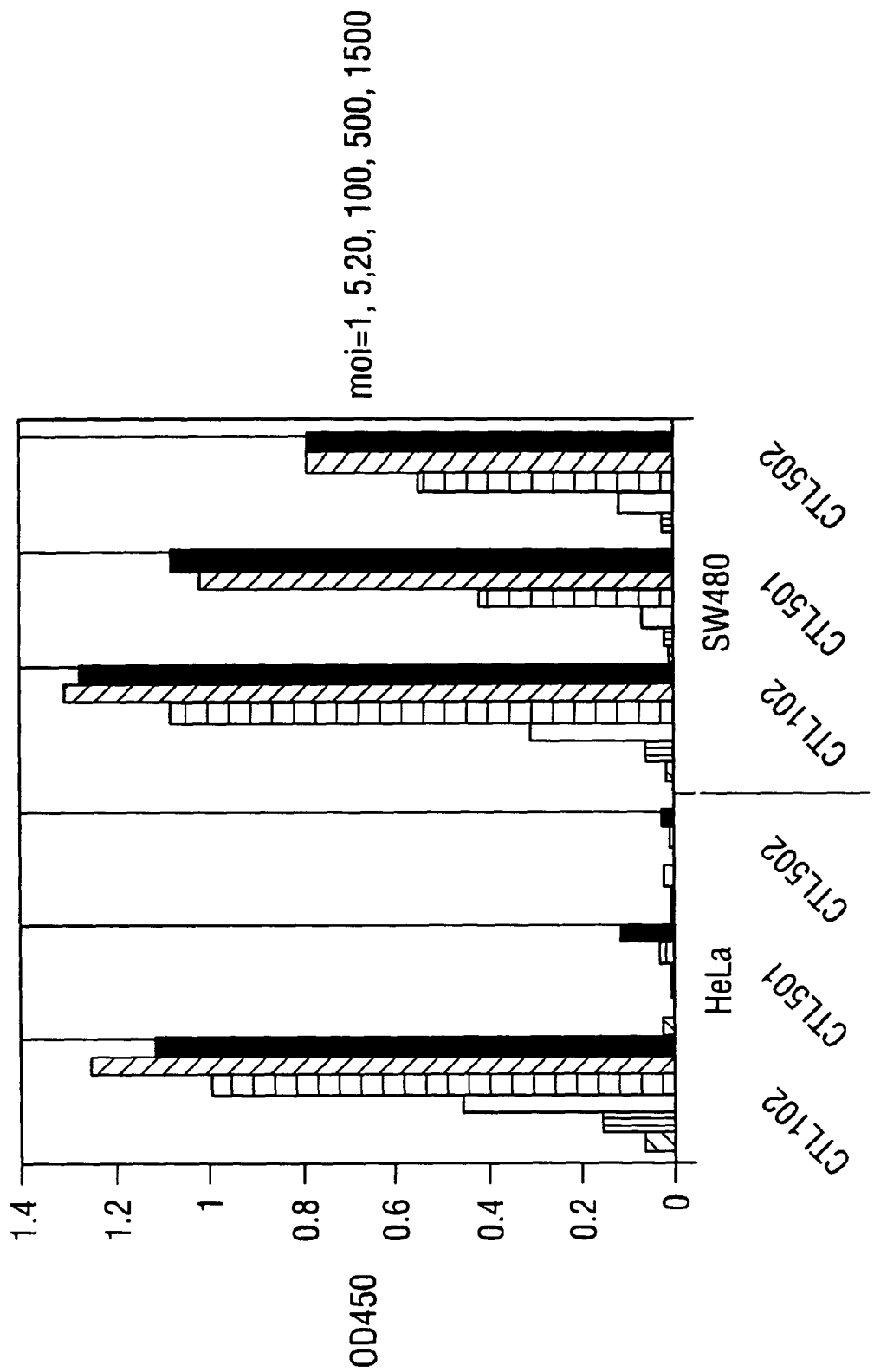

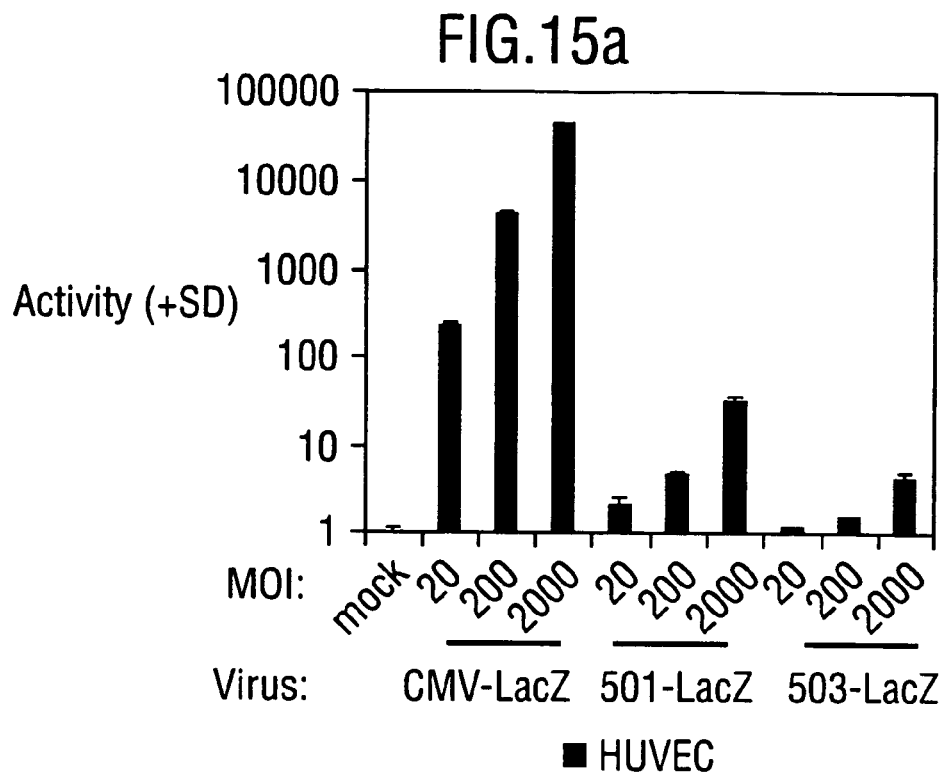
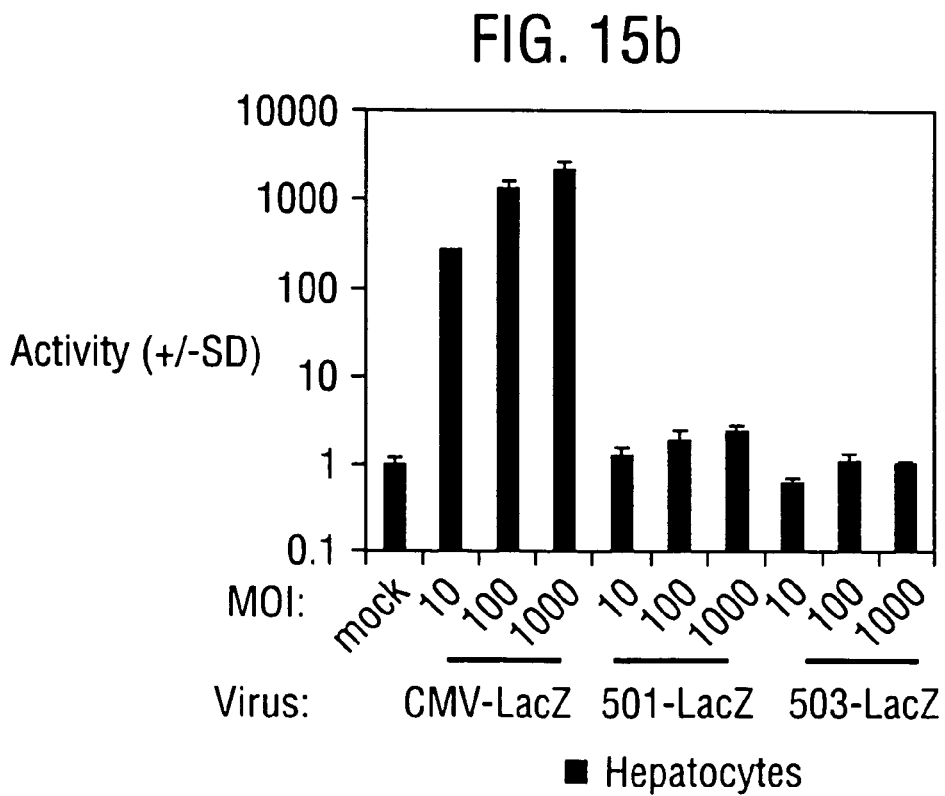

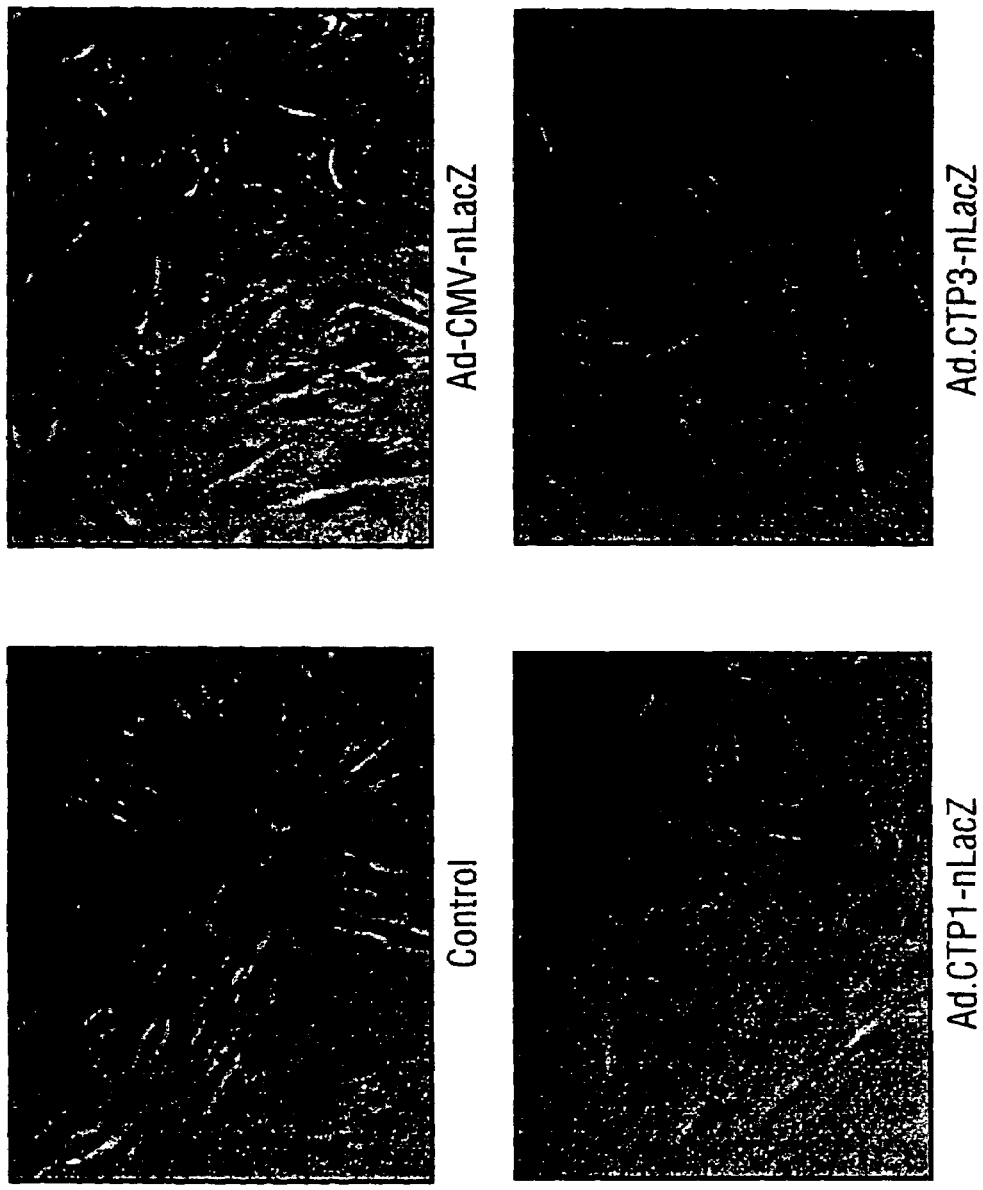

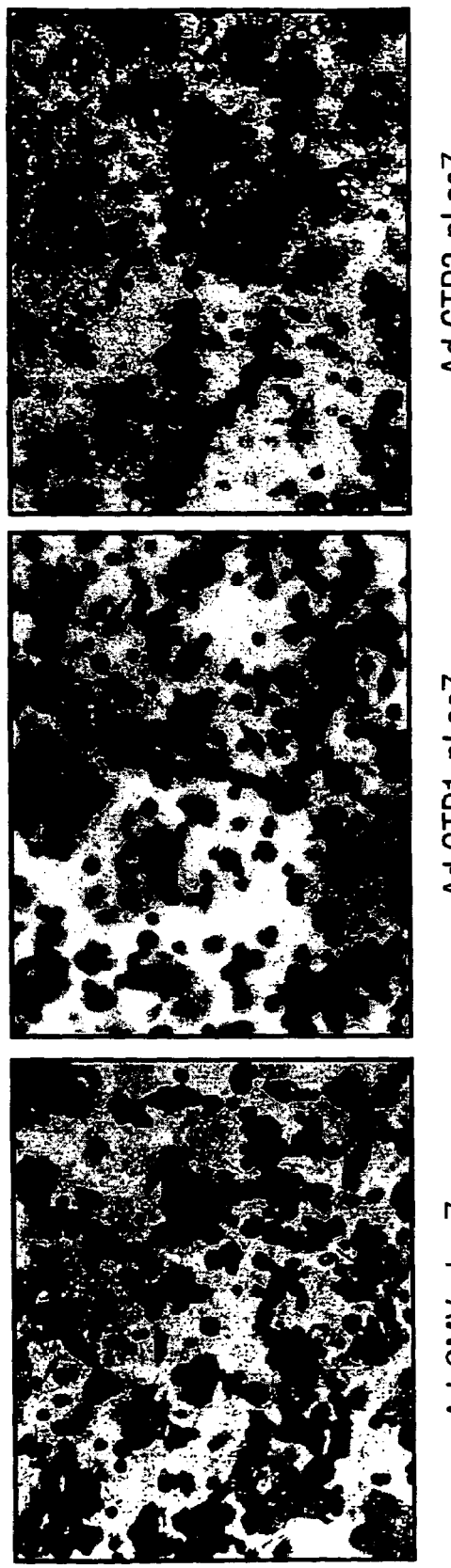
FIG. 15d – SW480 colorectal cancer positive control

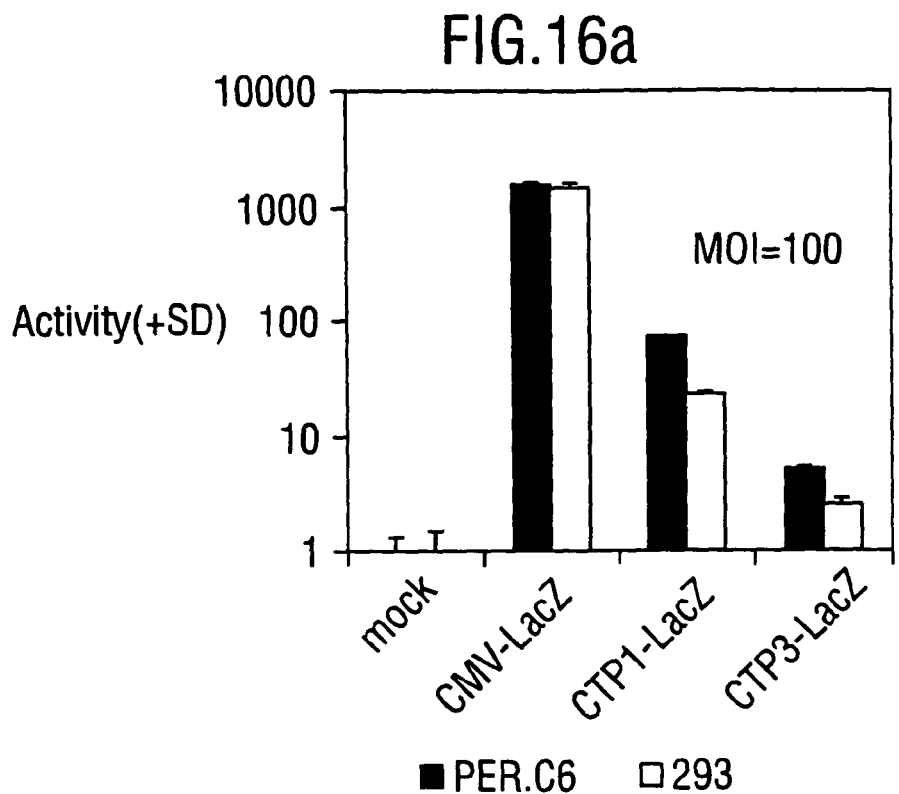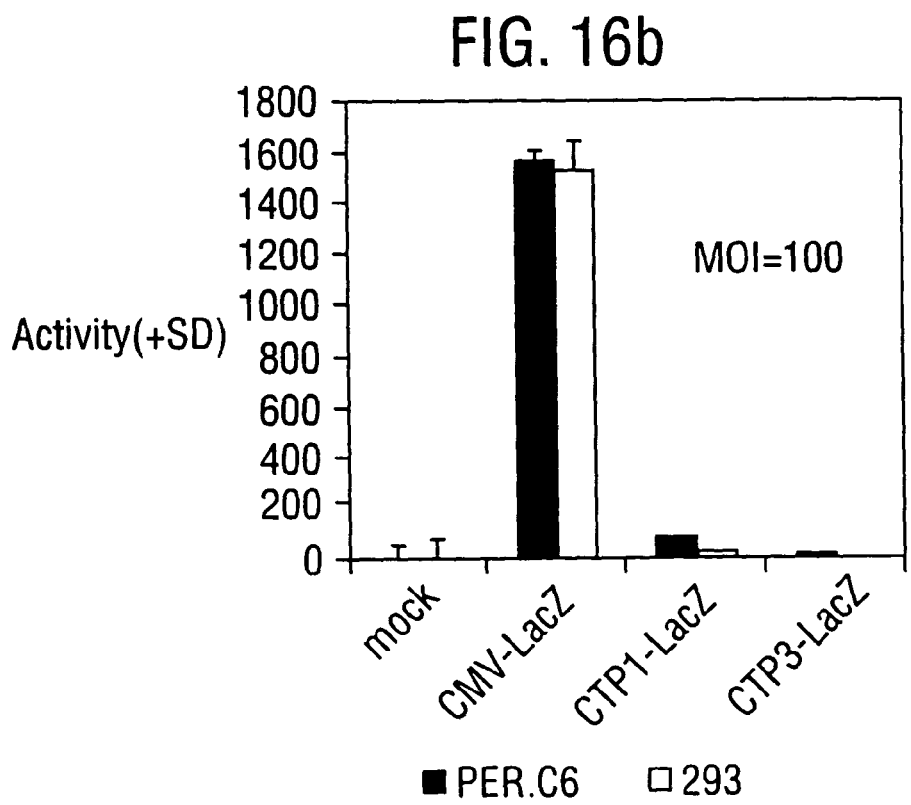

FIG.17
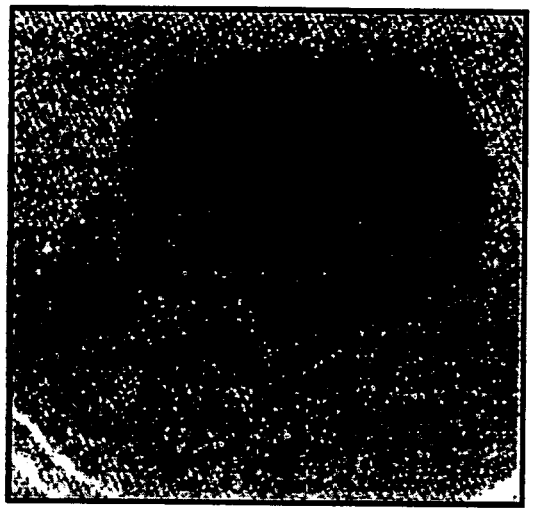
Control
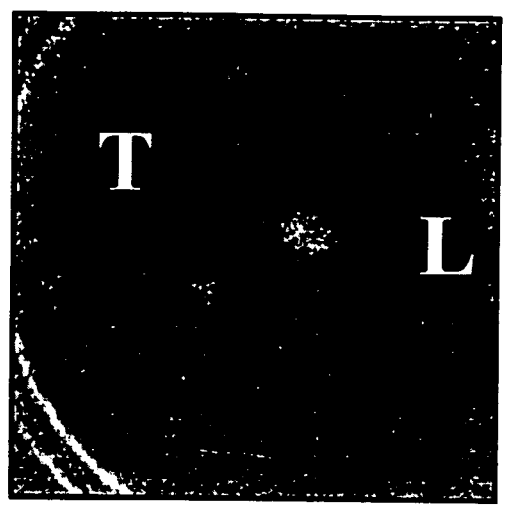
Ad-CMV-nLacZ
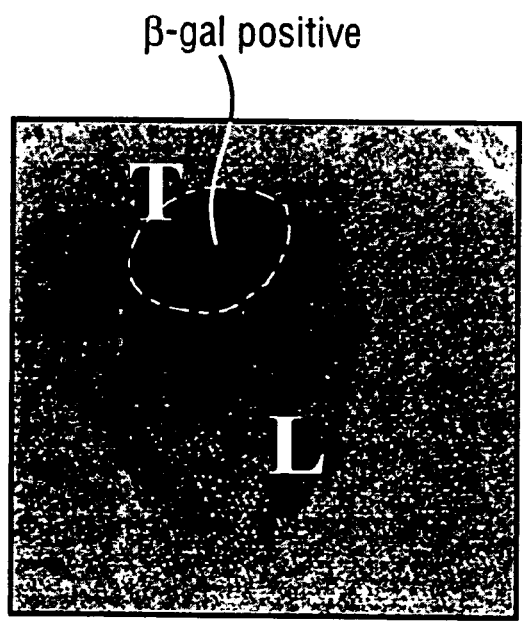
CTP1-nLacZ
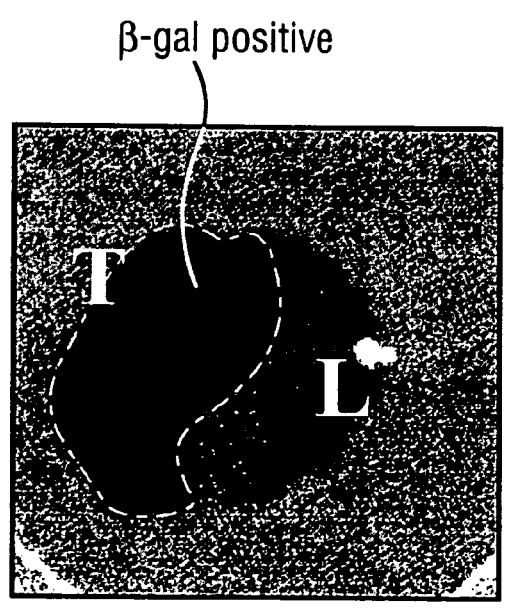
CTP3-nLacZ

SEQUENCE LISTING

<160> NUMBER OF SEQ ID NOS: 27

<210> SEQ ID NO 1
<211> LENGTH: 64
<212> TYPE: DNA
<213> ORGANISM: Artificial Sequence
<220> FEATURE:
<221> NAME/KEY: misc_feature
<223> OTHER INFORMATION: Synthetic Oligonucleotide
<220> FEATURE:
<221> NAME/KEY: misc_feature
<222> LOCATION: (1)..(1)
<223> OTHER INFORMATION: Phosphate modification

<400> SEQUENCE: 1
ctagcaagct tactagtcct ttgatcaaga gtcctacctt tgatctctaa atgcaccttt     60
gatc                                                                 64

<210> SEQ ID NO 2
<211> LENGTH: 72

```
<212> TYPE: DNA
<213> ORGANISM: Artificial Sequence
<220> FEATURE:
<221> NAME/KEY: misc_feature
<223> OTHER INFORMATION: Synthetic Oligonucleotide
<220> FEATURE:
<221> NAME/KEY: misc_feature
<222> LOCATION: (1)..(1)
<223> OTHER INFORMATION: Phosphate modification

<400> SEQUENCE: 2
actgaattcc ttgatcaaag gtgcatttag agatcaaagg taggactctt gatcaaagga      60
ctagtaagct tg                                                         72

<210> SEQ ID NO 3
<211> LENGTH: 60
<212> TYPE: DNA
<213> ORGANISM: Artificial Sequence
<220> FEATURE:
<221> NAME/KEY: misc_feature
<223> OTHER INFORMATION: Synthetic Oligonucleotide
<220> FEATURE:
<221> NAME/KEY: misc_feature
<222> LOCATION: (1)..(1)
<223> OTHER INFORMATION: Phosphate modification

<400> SEQUENCE: 3
aaggaattca gtcctttgat caagagtcct acctttgatc tctaaatgca cctttgatca     60

<210> SEQ ID NO 4
<211> LENGTH: 52
<212> TYPE: DNA
<213> ORGANISM: Artificial Sequence
<220> FEATURE:
<221> NAME/KEY: misc_feature
<223> OTHER INFORMATION: Synthetic Oligonucleotide
<220> FEATURE:
<221> NAME/KEY: misc_feature
<222> LOCATION: (1)..(1)
<223> OTHER INFORMATION: Phosphate modification

<400> SEQUENCE: 4
gatctgatca aaggtgcatt tagagatcaa aggtaggact cttgatcaaa gg             52

<210> SEQ ID NO 5
<211> LENGTH: 128
<212> TYPE: DNA
<213> ORGANISM: Artificial Sequence
<220> FEATURE:
<221> NAME/KEY: misc_feature
<223> OTHER INFORMATION: Synthetic Oligonucleotide
<220> FEATURE:
<221> NAME/KEY: misc_feature
<222> LOCATION: (1)..(1)
<223> OTHER INFORMATION: Phosphate modification

<400> SEQUENCE: 5
ctagcaagct tactagtcct tgatcaaga gtttcctacc tttgatctct aaattgcacc      60
tttgatcaag gaattcagtc ctttgatcaa gagtaaccta cctttgatct ctaaatgcac    120
ctttatca                                                            128

<210> SEQ ID NO 6
<211> LENGTH: 128
<212> TYPE: DNA
<213> ORGANISM: Artificial Sequence
<220> FEATURE:
<221> NAME/KEY: misc_feature
<223> OTHER INFORMATION: Synthetic Oligonucleotide
```

```
<220> FEATURE:
<221> NAME/KEY: misc_feature
<222> LOCATION: (1)..(1)
<223> OTHER INFORMATION: Phosphate modification

<400> SEQUENCE: 6
gatctgataa aggtgcattt agagatcaaa ggtaggttac tcttgatcaa aggactgaat      60
tccttgatca aggtgcaat ttagagatca aggtaggaa actcttgatc aaaggactag       120
taagcttg                                                              128

<210> SEQ ID NO 7
<211> LENGTH: 107
<212> TYPE: DNA
<213> ORGANISM: Artificial Sequence
<220> FEATURE:
<221> NAME/KEY: misc_feature
<223> OTHER INFORMATION: Synthetic Oligonucleotide
<220> FEATURE:
<221> NAME/KEY: misc_feature
<222> LOCATION: (1)..(1)
<223> OTHER INFORMATION: Phosphate modification

<400> SEQUENCE: 7
ctagcaagct tactagtcct tgatcaagc tacctttgat ctctagcacc tttgatcaag       60
agtcctttga tcaagcctac ctttgatctc taaatgcacc tttatca                   107

<210> SEQ ID NO 8
<211> LENGTH: 107
<212> TYPE: DNA
<213> ORGANISM: Artificial Sequence
<220> FEATURE:
<221> NAME/KEY: misc_feature
<223> OTHER INFORMATION: Synthetic Oligonucleotide
<220> FEATURE:
<221> NAME/KEY: misc_feature
<222> LOCATION: (1)..(1)
<223> OTHER INFORMATION: Phosphate modification

<400> SEQUENCE: 8
gatctgataa aggtgcattt agagatcaaa ggtaggcttg atcaaaggac tcttgatcaa      60
aggtgctaga gatcaaaggt agcttgatca aaggactagt aagcttg                   107

<210> SEQ ID NO 9
<211> LENGTH: 95
<212> TYPE: DNA
<213> ORGANISM: Artificial Sequence
<220> FEATURE:
<221> NAME/KEY: misc_feature
<223> OTHER INFORMATION: Synthetic Oligonucleotide
<220> FEATURE:
<221> NAME/KEY: misc_feature
<222> LOCATION: (1)..(1)
<223> OTHER INFORMATION: Phosphate Modification

<400> SEQUENCE: 9
ctagcaagct tactagtcct tgatcaata cctttgatct cacctttgat caagtccttt       60
gatcatacct tgatctcta aatgcaccct tatca                                 95

<210> SEQ ID NO 10
<211> LENGTH: 95
<212> TYPE: DNA
<213> ORGANISM: Artificial Sequence
<220> FEATURE:
<221> NAME/KEY: misc_feature
<223> OTHER INFORMATION: Synthetic Oligonucleotide
<220> FEATURE:
```

```
<221> NAME/KEY: misc_feature
<222> LOCATION: (1)..(1)
<223> OTHER INFORMATION: Phosphate modification

<400> SEQUENCE: 10
gatctgataa aggtgcattt agagatcaaa ggtatgatca aaggacttga tcaaaggtga      60
gatcaaaggt attgatcaaa ggactagtaa gcttg                                95

<210> SEQ ID NO 11
<211> LENGTH: 16
<212> TYPE: DNA
<213> ORGANISM: Adenovirus type 5

<400> SEQUENCE: 11
gggtatataa tgcgcc                                                     16

<210> SEQ ID NO 12
<211> LENGTH: 30
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 12
gaagatctcc ccttcttttc tatggttaag                                      30

<210> SEQ ID NO 13
<211> LENGTH: 29
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 13
gaagatctgc aatcattcgt ctgtttccc                                       29

<210> SEQ ID NO 14
<211> LENGTH: 30
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 14
gaagatctga tttggtcaat atgtgtacac                                      30

<210> SEQ ID NO 15
<211> LENGTH: 35
<212> TYPE: PRT
<213> ORGANISM: Artificial Sequence
<220> FEATURE:
<221> NAME/KEY: misc_feature
<223> OTHER INFORMATION: Synthetic Oligonucleotide

<400> SEQUENCE: 15

Lys Lys Lys Lys Lys Lys Gly Gly Phe Leu Gly Phe Trp Arg Gly Glu
1               5                   10                  15

Asn Gly Arg Lys Thr Arg Ser Ala Tyr Glu Arg Met Cys Asn Ile Leu
            20                  25                  30

Lys Gly Lys
        35
```

```
<210> SEQ ID NO 16
<211> LENGTH: 14
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 16
tacatctaga taat                                                         14

<210> SEQ ID NO 17
<211> LENGTH: 13
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 17
ttatctagat gta                                                          13

<210> SEQ ID NO 18
<211> LENGTH: 31
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 18
ctagtatcga ttgttaatta agggcgtggc c                                      31

<210> SEQ ID NO 19
<211> LENGTH: 31
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 19
ttaaggccac gcccttaatt aacaatcgat a                                      31

<210> SEQ ID NO 20
<211> LENGTH: 167
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 20
ttgagatgca gatcgcagat ctgataaagg tgcatttaga gatcaaaggt aggactcttg        60
atcaaaggac tgaattcctt gatcaaaggt gcatttagag atcaaaggta ggactctttg       120
atcaaaggga ctagtaagct tgctagcacg cgtaagagct cggtacc                     167

<210> SEQ ID NO 21
<211> LENGTH: 138
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 21
```

```
ggatgccaag cttttagct tccttagctc ctgaaaatct cgccaagctg atgaattcga      60
gctggcgcat tatataccct ctagagtcga cggatcgaga tctcgagccc gggctagcac    120
gcgtaagagc tcggtacc                                                  138

<210> SEQ ID NO 22
<211> LENGTH: 131
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 22
atcgagatct gataaaggtg catttagaga tcaaaggtag gttactcttt gaattcaggt     60
gcaatttaaa ggtaggaaac tcttgatcaa aggactagta agcttgctag cacgcgtaag   120
agctcggtac c                                                         131

<210> SEQ ID NO 23
<211> LENGTH: 125
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 23
atcgagatct gataaaggtg catttagaga tcaaaggtag gttactcttg atcaaaggac     60
tgaattcagg aaactcttga tcaaaggact agtaagcttg ctagcacgcg taagagctcg   120
gtacc                                                                125

<210> SEQ ID NO 24
<211> LENGTH: 121
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 24
atcgagatct gataaaggtg catttagaga tcaaaggtag tcacaggtgc aatttagaga     60
tcaaaggtag gaattgatca aggatagta agcttgctag cacgcgtaag agctcggtac    120
c                                                                    121

<210> SEQ ID NO 25
<211> LENGTH: 132
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 25
atcgagatct gataaaggtt cttgatcaaa ggactgaatt ccttgatcaa aggtgcaatt     60
tagagatcaa aggtaggaaa ctcttgatca aggactagt aagcttgcta gcacgcgtaa   120
gagctcggta cc                                                        132

<210> SEQ ID NO 26
<211> LENGTH: 150
<212> TYPE: DNA
```

-continued

```
<213> ORGANISM: Artificial Sequence
<220> FEATURE:
<221> NAME/KEY: misc_feature
<223> OTHER INFORMATION: Synthetic Oligonucleotide

<400> SEQUENCE: 26
atcgagatcg ataaaggtgc atttagacga tcaaaggtag gttactcttg atcaaaggaa      60
ttccttgatc aaaggtgcaa tttagagaag gtaggaaact cttgatcaaa ggactagtaa    120
gcttgctagc acgcgtaaga gctcggtacc                                      150

<210> SEQ ID NO 27
<211> LENGTH: 244
<212> TYPE: DNA
<213> ORGANISM: Artificial Sequence
<220> FEATURE:
<221> NAME/KEY: misc_feature
<223> OTHER INFORMATION: Synthetic Oligonucleotide

<400> SEQUENCE: 27
taccaacagt accggaatgc caagctagct ttttagcttc cttagctcct gaaaatctcg      60
ccaagctgat gaattcgagc tggcgcatta tataccctct gataaaggtg catttagaga    120
tcaaaggtat gatcaaagga cttgatcaaa ggtgagatca aaggtattga tcaaaggact    180
agagcttact tagatcgcag atctcgagcc cgggctagca cgcgtaagag ctcggtacct    240
atcg                                                                  244
```

GENE EXPRESSION USING T CELL FACTOR RESPONSIVE ELEMENT

CROSS REFERENCE TO RELATED APPLICATIONS

This application is a continuation application of U.S. application Ser. No. 09/798,128, filed Mar. 2, 2001, now U.S. Pat. No. 6,608,037, which claims priority under 35 U.S.C. § 119(a)–(d) of United Kingdom Application No. 0005099.7, filed Mar. 2, 2000 and also claims the benefit under 35 U.S.C. § 119(e) of U.S. application Ser. No. 60/187,465, filed Mar. 6, 2000, and claims benefit under 35 U.S.C. § 119(a)–(d) of PCT Application No. PCT/GB01/00856, filed Mar. 1, 2001, all applications incorporated herein by reference in their entireties.

BACKGROUND TO THE INVENTION

The present invention relates to a T cell factor (TCF)-responsive element, a gene and uses of the TCF-responsive element or nucleic acid construct in assays nucleic acid construct comprising a TCF-responsive element and a therapeutic and therapy.

TCFs are a family of transcription factors within the High Mobility Group (HMG) of DNA-binding proteins (Love et al., Nature, 376, 791–795,1995). The family includes TCF-1, TCF-3 and TCF-4 which are described in van der Wetering et al, (EMBO J., 10, 123–132, 1991), EP-A-0 939 122 and Korinek et al. (Science, 275, 1784–1787, 1997). TCF-4 has been shown to be involved in tumorigenesis related to Wnt/Wingless signalling. TCF and LEF-1 (lymphoid enhancer factor-1) are considered to mediate a nuclear response to Wnt signals by interacting with β-catenin. Wnt signalling and other cellular events that increase the stability of β-catenin are considered to result in transcriptional activation of genes by LEF-1 and TCF proteins in association with β-catenin. In the absence of Wnt signalling, LEF-1/TCF proteins repress transcription in association with Groucho and CBP (CREB binding protein).

In the absence of Wnt signalling, β-catenin is found in two distinct multiprotein complexes. One complex, located at the plasma membrane, couples cadherins (calcium dependent adhesion molecules) with the actin cytoskeleton whereas the other complex (containing the proteins adenomatous polyposis coli protein (APC), axin and glycogen synthase kinase 3β (GSK3β)) targets β-catenin for degradation. Wnt signalling antagonises the APC-axin-GSK3β complex, resulting in an increase in the pool of free cytoplasmic β-catenin. The free cytoplasmic β-catenin can translocate to the nucleus where it binds LEF-1/TCF factors and activates Wnt target genes. The regulation of LEF-1/TCF transcription factors by Wnt and other signals is discussed in Eastman et al, (Current Opin. Cell Biology, 11, 233–240,1999).

The APC gene is a tumour supressor gene that is inactivated in most colorectal cancers. Mutations of APC are considered to cause the accumulation of free β-catenin, which then binds TCF causing increased transcriptional activation of genes including genes important for cell proliferation (e.g. cyclin D1 (Tetsu et al., Nature 398, 422–426, 1999 and Shtutman et al., PNAS USA, 96, 5522–5527, 1999) and c-myc (He et al., Science, 281, 1509–1512, 1998)). The involvement of APC in tumour development is discussed in He et al, (supra).

TCFs are known to recognise and bind TCF binding elements which have the nucleotide sequence CTTTGNN, wherein N indicates A or T (van der Wetering et al, supra).

TCF reporter genes have been constructed and are described in Korinek et al, (Science, 275, 1784–1787,1997), Morin et al, (Science, 275,1787–1790, 1997), EP-A-0 939 122 and WO 98/41631. The TCF reporter gene is said to comprise three TCF binding elements upstream of either a minimal c-Fos promoter driving luciferase expression or a minimal herpes virus thymidine kinase promoter driving chloramphenicol acetyl-transferase expression. He et al (supra) discloses TCF reporter gene constructs comprising four TCF binding elements inserted into pBV-Luc.

There is a need for an effective treatment of cancers associated with a deregulation of the Wnt signalling pathway. Such cancers include most colorectal cancers, approximately 30% of melanomas and some breast, prostate and hepatocellular carcinomas.

There is also a need for a TCF response element which when linked to an expressible gene gives improved levels of expression and specificity.

SUMMARY OF THE INVENTION

The present invention provides a nucleic acid construct comprising:
 a TCF response element comprising:
  at least one TCF binding element having the sequence CTTTGNN, wherein N is A or T; and
  a promoter,
 and an expressible therapeutic gene operably linked to the TCF response element, wherein the TCF response element enables inducible expression of the operably linked therapeutic gene.

The term "inducible expression" as used herein means the level of expression obtained using the TCF response element is induced (i.e. increased) when one or more TCF/β catenin heterodimers binds to one or more of the TCF binding elements. Preferably the level of expression is increased by at least 15 fold, more preferably at least 25 fold and most preferably at least 30 fold.

The term "operably linked" as used herein refers to a cis-linkage in which the gene is subject to expression under control of the TCF response element.

The expressible gene comprises the necessary elements enabling gene expression when operably linked to the TCF response element, such as splice acceptor sequences, internal ribosome entry site sequences (IRES) and transcription stop sites. Such elements are well known to those skilled in the art.

It has been found that by using the nucleic acid construct of the present invention that expression of the operably linked therapeutic gene is only induced when TCF/β catenin heterodimers are present and capable of activating transcription. As cells that have become cancerous due to the deregulation of the Wnt signalling pathway have TCF/β catenin heterodimers, which activate transcription, expression of the therapeutic gene will be induced. Accordingly, the nucleic acid construct of the present invention acts as a tumour selective promoter.

The nucleic acid construct of the present invention exhibits highly selective expression in that it gives no induction of expression of an operably linked gene above the background level in the absence of TCF/β catenin heterodimers or a functionally equivalent transcription activating factor.

The therapeutic gene can be any gene that on expression gives a therapeutic benefit. Preferred therapeutic genes include genes encoding toxins such as ricin and diphtheria toxin, and prodrug activating enzymes such as nitroreductases that activate CB1954, cytosine deaminase which activates 5-fluorocytosine, cytochrome P-450 which activates cyclophosphamide and paracetamol, and thymidine kinase which activates ganciclovir. Preferably the therapeutic gene encodes a nitroreductase. Suitable nitroreductases are described in EP-A-0638123 and Watanabe et al, (NAR, 18, 1059,1990). Other preferred therapeutic gene include genes encoding immunomodulatory agents such as IL-2, IL-12, GMCSF, B7-1 and B7-2 co-stimulatory molecules; genes encoding tumour suppressers such as RB, p53 and p16; and genes encoding apoptotic genes such as Bax, FasL and caspases.

The promoter can be any promoter that gives a desired level of expression of the operably linked gene. Suitable promoters include the SV40 promoter, the E1B promoter, and the c-Fos promoter. Preferably the promoter is the basal TATA box of the E1B promoter.

Preferably the TCF response element contains at least three and more preferably at least five TCF binding elements. It has been found that by using at least three and more preferably at least five TCF binding elements that an unexpected increase in expression can be obtained compared to a TCF response element containing fewer binding elements. This increase in expression is desirable for the production of a therapeutically effective amount of an encoded product.

Preferably the TCF response element comprises between 5 and 15 TCF binding elements, more preferably between 5 and 10 TCF binding elements and most preferably 5 TCF binding elements.

The TCF binding elements are preferably separated from each other by between 3 and 20 nucleotides, more preferably by between 3 and 14 and most preferably by between 10 and 12 nucleotides.

It is further preferred that the TCF binding elements are so spaced from each other as to be equally distributed radially around the DNA helix, especially when the promoter is the E1B promoter.

It is preferred that the TCF binding element closest to the promoter is between 140 and 10 nucleotides from the TATA box of the promoter. It is further preferred that the TCF binding element closest to the promoter is between 100 and 10 nucleotides, more preferably between 50 and 10 and most preferably between 30 and 15 nucleotides from the TATA box of the promoter.

In one preferred embodiment the TCF binding elements are separated from each other by between 3 or 4 nucleotides and the TCF binding element closest to the promoter is 25 nucleotides from the TATA box of the promoter.

The TCF binding elements preferably have the nucleotide sequence CTTTGAT.

The TCF binding elements can be in either orientation with respect to the promoter, namely 5' to 3' or 3' to 5'.

The present invention also provides a nucleic acid construct designated herein as 5merTCF-E1BTATA, which is shown schematically in FIG. 6 and described in the materials and method section below.

The present invention also provides a TCF response element comprising:
  at least five TCF binding elements; and
  a promoter sequence, wherein the TCF response element when operably linked to an expressible gene gives inducible expression of the operably linked gene.

The TCF response element comprising at least five TCF binding elements can be used to obtain inducible expression of any operably linked gene such as a reporter gene or a therapeutic gene. Suitable reporter genes include luciferase, β-galactosidase and chloramphenicol acetyl transferase.

The TCF response element comprising at least five TCF binding elements has been found to give improved (i.e. increased) levels of expression of an operably linked gene compared to a TCF response element comprising less than 5 TCF binding elements.

The TCF binding elements and the promoter of the TCF response element comprising at least 5 TCF binding elements are as defined above.

The present invention also provides a TCF reporter construct comprising the TCF response element having at least 5 TCF binding elements operably linked to a reporter gene.

The present invention also provides the use of the TCF reporter construct of the present invention in a method of identifying candidate drugs for use in the treatment of cancers associated with the deregulation of the Wnt signalling pathway comprising the steps of:
  contacting the TCF reporter construct with a test compound under conditions in which the reporter gene is transcribed; and
  measuring the transcription of the reporter gene;

wherein a test compound which inhibits transcription of the reporter gene is a candidate drug for cancer treatment.

Preferably the step of contacting the TCF reporter construct is performed in the presence of a lysate from a cell with a deregulated Wnt signalling pathway.

The present invention also provides a vector comprising the nucleic acid construct of the present invention or the TCF responsive element having at least five TCF binding elements of the present invention operably linked to an expressible gene.

The vector may be any vector capable of transferring DNA to a cell. Preferably, the vector is an integrating vector or an episomal vector.

Preferred integrating vectors include recombinant retroviral vectors. A recombinant retroviral vector will include DNA of at least a portion of a retroviral genome which portion is capable of infecting the target cells. The term "infection" is used to mean the process by which a virus transfers genetic material to its host or target cell. Preferably, the retrovirus used in the construction of a vector of the invention is also rendered replication-defective to remove the effect of viral replication of the target cells. In such cases, the replication-defective viral genome can be packaged by a helper virus in accordance with conventional techniques. Generally, any retrovirus meeting the above criteria of infectiousness and capability of functional gene transfer can be employed in the practice of the invention.

Suitable retroviral vectors include but are not limited to pLJ, pZip, pWe and pEM, well known to those of skill in the art. Suitable packaging virus lines for replication-defective retroviruses include, for example, ΨCrip, ΨCre, Ψ2 and ΨAm.

Other vectors useful in the present invention include adenovirus, adeno-associated virus, SV40 virus, vaccinia virus, HSV and poxvirus vectors. A preferred vector is the adenovirus. Adenovirus vectors are well known to those skilled in the art and have been used to deliver genes to numerous cell types, including airway epithelium, skeletal muscle, liver, brain and skin (Hitt, M M, Addison C L and Graham, F L (1997) Human adenovirus vectors for gene transfer into mammalian cells. *Advances in Pharmacology*, 40: 137–206; and Anderson W F (1998) Human gene therapy. *Nature*, 392: (6679 Suppl): 25–30).

A further preferred vector is the adeno-associated (AAV) vector. AAV vectors are well known to those skilled in the art and have been used to stably transduce human T-lymphocytes, fibroblasts, nasal polyp, skeletal muscle, brain, erythroid and haematopoietic stem cells for gene therapy applications (Philip et al., 1994, Mol. Cell. Biol., 14, 2411–2418; Russell et al, 1994, PNAS USA, 91, 8915–8919; Flotte et al., 1993, PNAS USA, 90, 10613–10617; Walsh et al., 1994, PNAS USA, 89, 7257–7261; Miller et al., 1994, PNAS USA, 91, 10183–10187; Emerson, 1996, Blood, 87, 3082–3088). International Patent Application WO 91/18088 describes specific MV based vectors.

Preferred episomal vectors include transient non-replicating episomal vectors and self-replicating episomal vectors with functions derived from viral origins of replication such as those from EBV, human papovavirus (BK) and BPV-1. Such integrating and episomal vectors are well known to those skilled in the art and are fully described in the body of literature well known to those skilled in the art. In particular, suitable episomal vectors are described in WO98/07876.

Mammalian artificial chromosomes can also be used as vectors in the present invention. The use of mammalian artificial chromosomes is discussed by Calos (1996, TIG, 12, 463–466).

In a preferred embodiment, the vector of the present invention is a plasmid. The plasmid may be is a non-replicating, non-integrating plasmid.

The term "plasmid" as used herein refers to any nucleic acid encoding an expressible gene and includes linear or circular nucleic acids and double or single stranded nucleic acids. The nucleic acid can be DNA or RNA and may comprise modified nucleotides or ribonucleotides, and may be chemically modified by such means as methylation or the inclusion of protecting groups or cap- or tail structures.

A non-replicating, non-integrating plasmid is a nucleic acid which when transfected into a host cell does not replicate and does not specifically integrate into the host cell's genome (i.e. does not integrate at high frequencies and does not integrate at specific sites).

Replicating plasmids can be identified using standard assays including the standard replication assay of Ustav et al., EMBO J., 10, 449–457, 1991.

The present invention also provides a host cell transfected with the vector of the present invention. The host cell may be any mammalian cell. Preferably the host cell is a rodent or mammalian cell.

Numerous techniques are known and are useful according to the invention for delivering the vectors described herein to cells, including the use of nucleic acid condensing agents, electroporation, complexing with asbestos, polybrene, DEAE cellulose, Dextran, liposomes, cationic liposomes, lipopolyamines, polyornithine, particle bombardment and direct microinjection (reviewed by Kucherlapati and Skoultchi, Crit. Rev. Biochem. 16:349–379 (1984); Keown et al., Methods Enzymol. 185:527 (1990)).

A vector of the invention may be delivered to a host cell non-specifically or specifically (i.e., to a designated subset of host cells) via a viral or non-viral means of delivery. Preferred delivery methods of viral origin include viral particle-producing packaging cell lines as transfection recipients for the vector of the present invention into which viral packaging signals have been engineered, such as those of adenovirus, herpes viruses and papovaviruses. Preferred non-viral based gene delivery means and methods may also be used in the invention and include direct naked nucleic acid injection, nucleic acid condensing peptides and non-peptides, cationic liposomes and encapsulation in liposomes.

The direct delivery of vector into tissue has been described and some short-term gene expression has been achieved. Direct delivery of vector into muscle (Wolff et al., Science, 247, 1465–1468, 1990) thyroid (Sykes et al., Human Gene Ther., 5, 837–844, 1994) melanoma (Vile et al., Cancer Res., 53, 962–967, 1993), skin (Hengge et al., Nature Genet, 10, 161–166, 1995), liver (Hickman et al., Human Gene Therapy, 5,1477–1483, 1994) and after exposure of airway epithelium (Meyer et al., Gene Therapy, 2, 450–460, 1995) is clearly described in the prior art.

Various peptides derived from the amino acid sequences of viral envelope proteins have been used in gene transfer when co-administered with polylysine DNA complexes (Plank et al., J. Biol. Chem. 269:12918–12924 (1994)); Trubetskoy et al., Bioconjugate Chem. 3:323–327 (1992); WO 91/17773; WO 92/19287; and Mack et al., Am. J. Med. Sci. 307:138–143 (1994)) suggest that co-condensation of polylysine conjugates with cationic lipids can lead to improvement in gene transfer efficiency. International Patent Application WO 95/02698 discloses the use of viral components to attempt to increase the efficiency of cationic lipid gene transfer.

Nucleic acid condensing agents useful in the invention include spermine, spermine derivatives, histones, cationic peptides, cationic non-peptides such as polyethyleneimine (PEI) and polylysine. 'Spermine derivatives' refers to analogues and derivatives of spermine and include compounds as set forth in International Patent Application WO 93/18759 (published Sep. 30, 1993).

Disulphide bonds have been used to link the peptidic components of a delivery vehicle (Cotten et al., Meth. Enzymol. 217:618–644 (1992)); see also, Trubetskoy et al. (supra).

Delivery vehicles for delivery of DNA constructs to cells are known in the art and include DNA/poly-cation complexes which are specific for a cell surface receptor, as described in, for example, Wu and Wu, J. Biol. Chem. 263:14621 (1988); Wilson et al., J. Biol. Chem. 267:963–967 (1992); and U.S. Pat. No. 5,166,320).

Delivery of a vector according to the invention is contemplated using nucleic acid condensing peptides. Nucleic acid condensing peptides, which are particularly useful for condensing the vector and delivering the vector to a cell, are described in International Patent Application WO 96/41606. Functional groups may be bound to peptides useful for delivery of a vector according to the invention, as described in WO 96/41606. These functional groups may include a ligand that targets a specific cell-type such as a monoclonal antibody, insulin, transferrin, asialoglycoprotein, or a sugar. The ligand thus may target cells in a non-specific manner or in a specific manner that is restricted with respect to cell type.

The functional groups also may comprise a lipid, such as palmitoyl, oleyl, or stearoyl; a neutral hydrophilic polymer such as polyethylene glycol (PEG), or polyvinylpyrrolidine (PVP); a fusogenic peptide such as the HA peptide of influenza virus; or a recombinase or an integrase. The functional group also may comprise an intracellular trafficking protein such as a nuclear localisation sequence (NLS), an endosome escape signal such as a membrane disruptive peptide, or a signal directing a protein directly to the cytoplasm.

The present invention also provides the nucleic acid construct, vector or host cell of the present invention for use in therapy.

Preferably, the nucleic acid construct, vector or host cell is used in the treatment of cancer.

The present invention also provides the use of the nucleic acid construct, vector or host cell of the present invention in the manufacture of a composition for use in the treatment of cancer.

The present invention also provides a method of treatment, comprising administering to a patient in need of such treatment an effective dose of the nucleic acid construct, vector or host cell of the present invention. Preferably, the patient is suffering from cancer.

Preferably, the cancer is any cancer associated with the deregulation of the Wnt signalling pathway such as colorectal cancer, melanomas, breast, prostate and hepatocellular carcinomas.

The present invention also provides a pharmaceutical composition comprising the nucleic acid construct, vector or host cell of the present invention in combination with a pharmaceutically acceptable excipient.

The pharmaceutical compositions of the present invention may comprise the nucleic acid construct, vector or host cell of the present invention, if desired, in admixture with a pharmaceutically acceptable carrier or diluent, for therapy to treat a disease.

The nucleic acid construct, vector or host cell of the invention or the pharmaceutical composition may be administered via a route which includes systemic, intramuscular, subcutaneous, intradermal, intravenous, aerosol, oral (solid or liquid form), topical, ocular, as a suppository, intraperitoneal and/or intrathecal and local direct injection.

The exact dosage regime will, of course, need to be determined by individual clinicians for individual patients and this, in turn, will be controlled by the exact nature of the protein expressed by the therapeutic gene and the type of tissue that is being targeted for treatment.

The dosage also will depend upon the disease indication and the route of administration.

The amount of nucleic acid construct or vector delivered for effective treatment according to the invention will preferably be in the range of between about 50 ng–1000 μg of vector DNA/kg body weight; and more preferably in the range of between about 1–100 μg vector DNA/kg.

Although it is preferred according to the invention to administer the nucleic acid construct, vector or host cell to a mammal for in vivo cell uptake, an ex vivo approach may be utilised whereby cells are removed from an animal, transduced with the nucleic acid construct or vector, and then re-implanted into the animal. The liver, for example, can be accessed by an ex vivo approach by removing hepatocytes from an animal, transducing the hepatocytes in vitro and re-implanting the transduced hepatocytes into the animal (e.g., as described for rabbits by Chowdhury et al., Science 254:1802–1805, 1991, or in humans by Wilson, Hum. Gene Ther. 3:179–222, 1992). Such methods also may be effective for delivery to various populations of cells in the circulatory or lymphatic systems, such as erythrocytes, T cells, B cells and haematopoietic stem cells.

The present invention also provides a composition for delivering the nucleic acid construct of the present invention or the TCF response element comprising at least 5 TCF binding elements of the present invention operably linked to an expressible gene to a cell.

A BRIEF DESCRIPTION OF THE FIGURES

FIGS. 1a–c show the results of transient transfections of HeLa, HepG2 and SW480 cells with the Tcf responsive luciferase reporter construct "5merTcf-SV40-Luc" (CTL501) (FIG. 1a). The numbers indicate the numbers of base pairs between the Tcf sites. The nucleotide sequence of 5merTCF-SV40 antisense strand (SEQ ID NO: 20) is shown in FIG. 1c. The sequences underlined and in italics are active TCF sites. The sequence just underlined is a mutated TCF site. The sequences in bold are the Bg/II, NheI and KpnI recognition sites. Cells were transfected with equimolar amounts (about 1 μg each) of the Tcf-responsive and control luciferase reporter constructs as indicated in FIG. 1b. "SV40p" contains the SV40 promoter only; "SV40 e/p" contains both the SV40 promoter and enhancer; "CMV" contains the cytomegalovirus enhancer/promoter. Data are expressed as fold activation with respect to the activity of the SV40 promoter set as 1. The mean value and SD from two independent transfections are shown. This result is representative of three independent experiments.

Figure 2B:
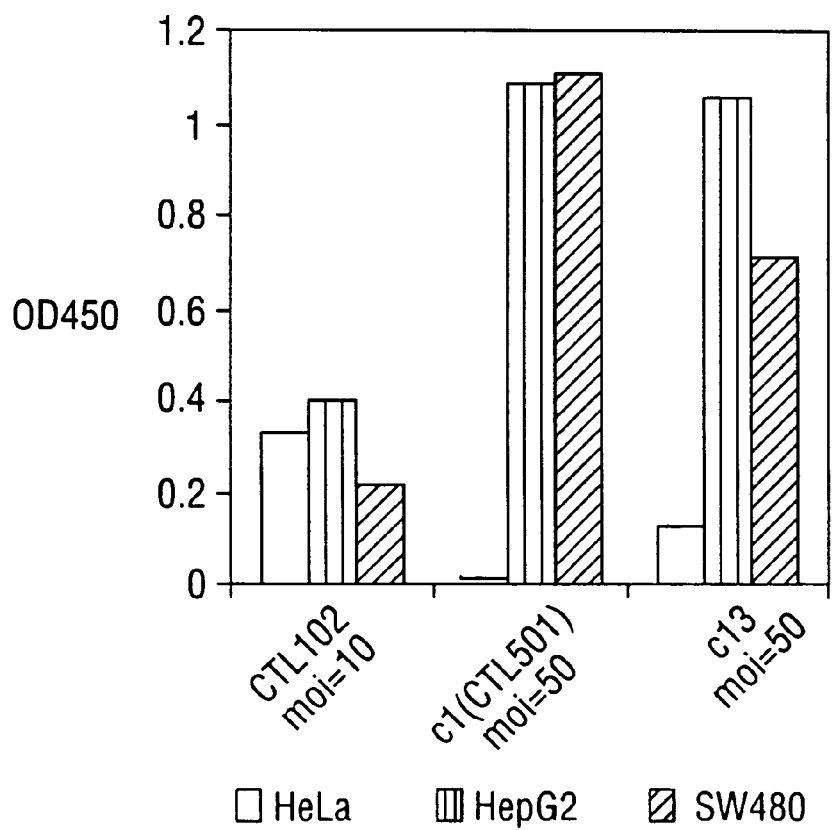

FIGS. 2a–b show the quantitation of nitroreductase (NTR) expressed by HeLa, HepG2 and SW480 cells infected with CTL102 or with CTL501. Cells were infected at the indicated multiplicities of infection (moi, pfu/cell) with either CTL102, which expresses NTR from the CMV enhancer/promoter, c1 (CTL501), which contains the 5merTcf-SV40-NTR cassette in a left to right orientation or with c13, which contains the same cassette but in the right to left orientation. Cytoplasmic extracts were prepared two days later and assayed for NTR expression by ELISA (see materials and methods). Infections were done in duplicate. The mean NTR expression level from a representative experiment is shown.

FIG. 3 shows the antitumour efficacy of CTL501/CB1954 against HepG2 xenograft tumours in nude mice. Groups of six tumours ranging in size from 20–80 mm$^2$ cross sectional area were injected with approximately $10^{10}$ viral particles as a single injection. Prodrug administration and tumour measurement are described in materials and methods.

FIG. 4 summarises the results of NTR immunostaining of subcutaneous SW480 xenografts in nude mice after a single injection of CTL501 or CTL102 (1.5×$10^{10}$ particles in 20 μl of 5% sucrose, 25 mM Tris-HCl, pH 7.4). The tumours were excised after 48 hours and monitored for NTR expression as described in the materials and methods section. The average percentage NTR positive cells from 3 consecutive sections are shown for each dissected tumour.

Figure 5:
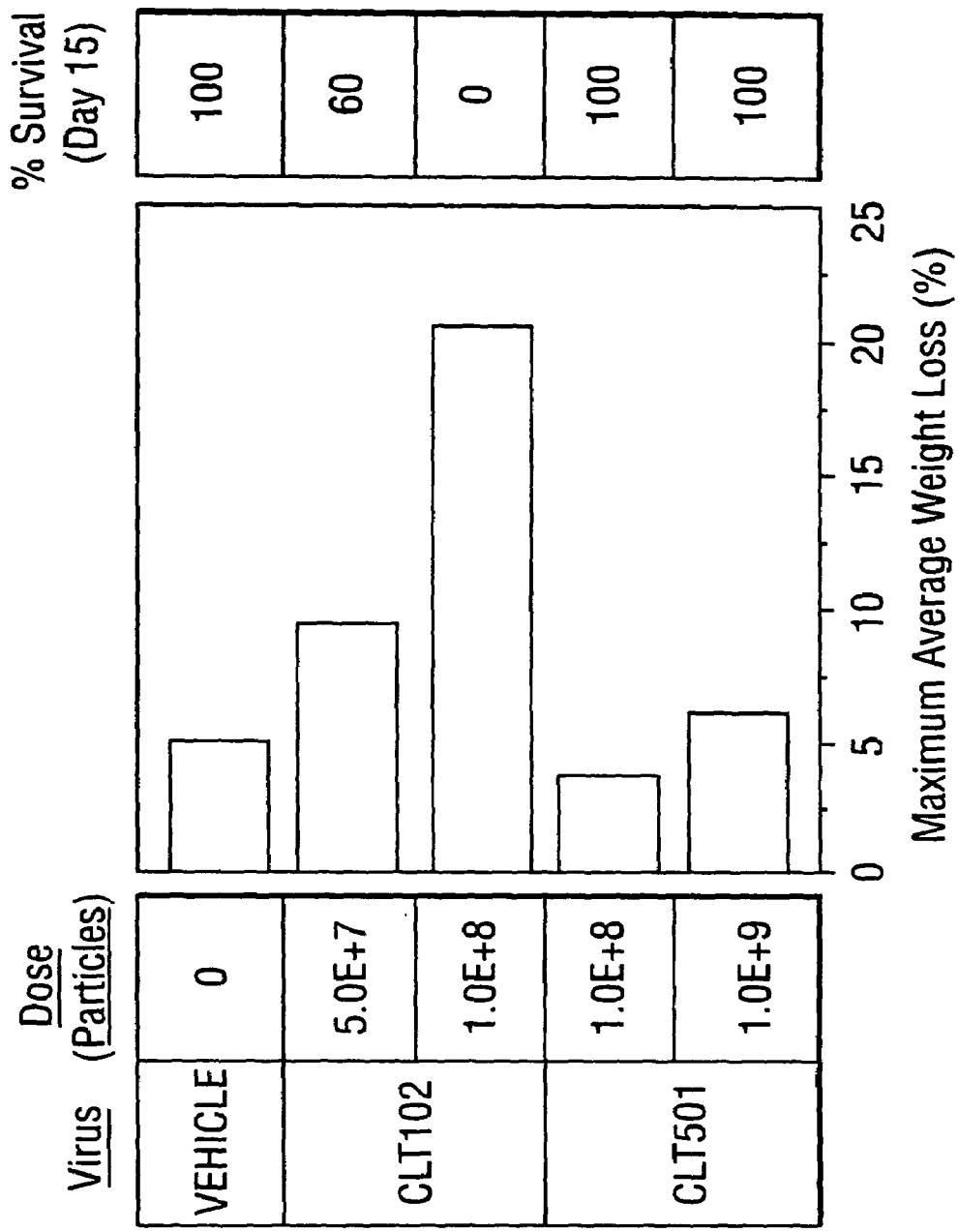

FIG. 5 shows a comparison of the in vivo toxicity of CTL501 compared to CTL102 following systemic administration and prodrug treatment. Nude mice were intravenously injected (tail vein) with the indicated number of viral particles. After 48 hours CB1954 was given intraperitoneally for 5 consecutive days at 20 mg/kg body weight. The figure shows the maximum average weight loss (%) during the monitoring period (day 1–15) for each animal group (4 animals per group) and percentage of surviving animals for each treatment group after 15 days.

FIGS. 6*a-c* show the results of transient transfections of HeLa and SW480 cells with the Tcf responsive luciferase reporter construct 5merTcf-E1BTATA-Luc (CTL502) (FIG. 6*a*). The nucleotide sequence of E1BTATA antisense strand (SEQ ID NO:21) is shown in FIG. 6*c*. The sequence underlined and in italics is the E1B TATA box. The sequences in bold are the HindIII, Bg/II, NheI and KpnI recognition sites. Cells were transfected with equimolar (about 1 µg each) amounts of several luciferase reporter constructs as indicated in FIG. 6*b*. pGL3 basic contains a promoterless luc cDNA; "E1B" contains the Ad5 E1BTATA box upstream of the luc cDNA; 5merTcf-SV40 (CTL501) is described in FIG. 1*a*. Data are expressed as fold activation compared to the activity of pGL3basic set as 1. The mean value and SD of duplicate transfections are shown. The data are representative of three independent experiments.

Figure 7:
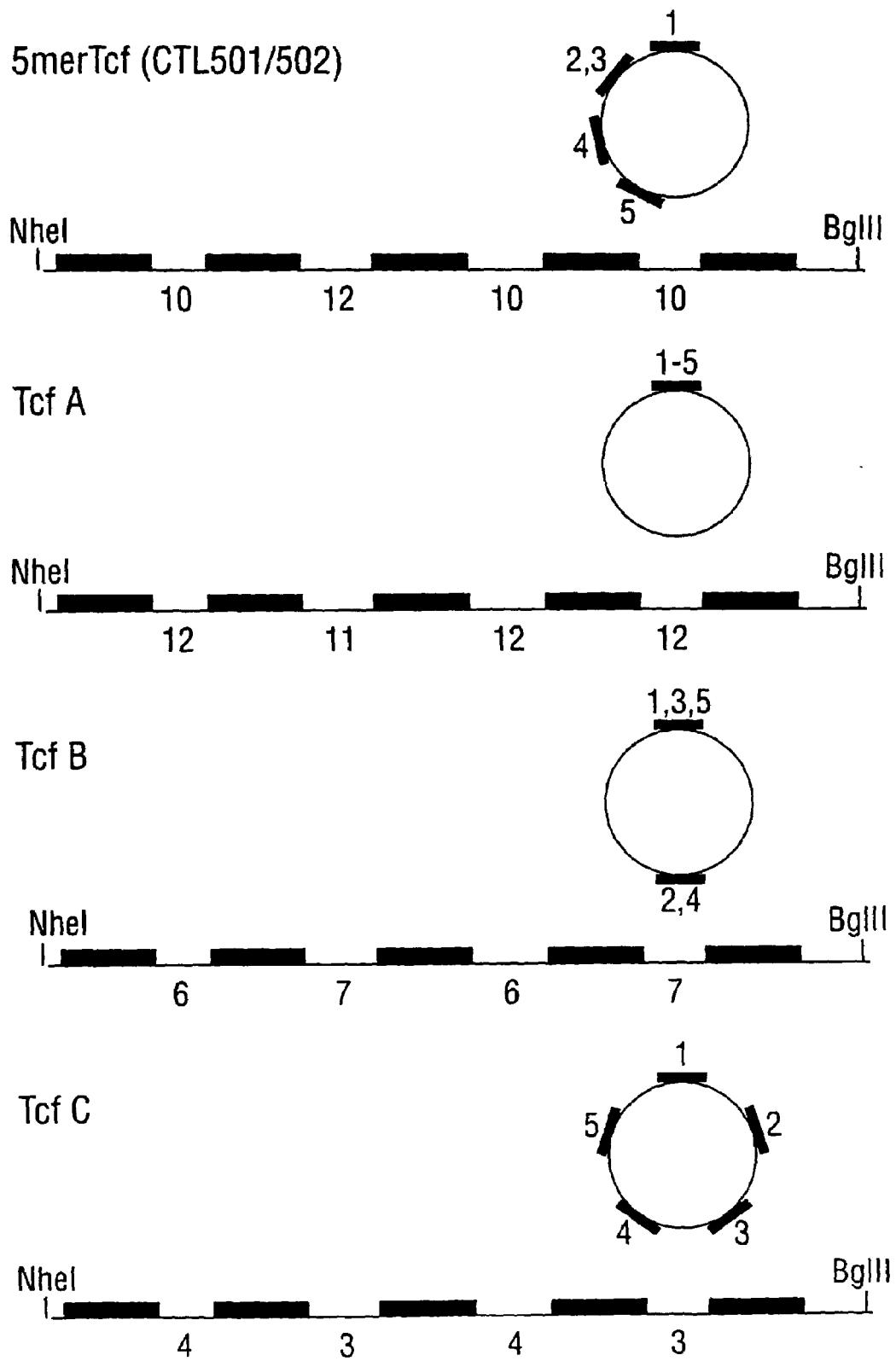

FIG. 7 shows, in schematic form, the four different arrangements of 5 Tcf binding elements that were evaluated in the work described in this document. For each construct the number of base pairs between the binding sites is shown, as well as the two dimensional arrangement of the sites along the DNA helix based on the assumption that 10.4 bp correspond to a complete turn of the helix.

Figure 8A:
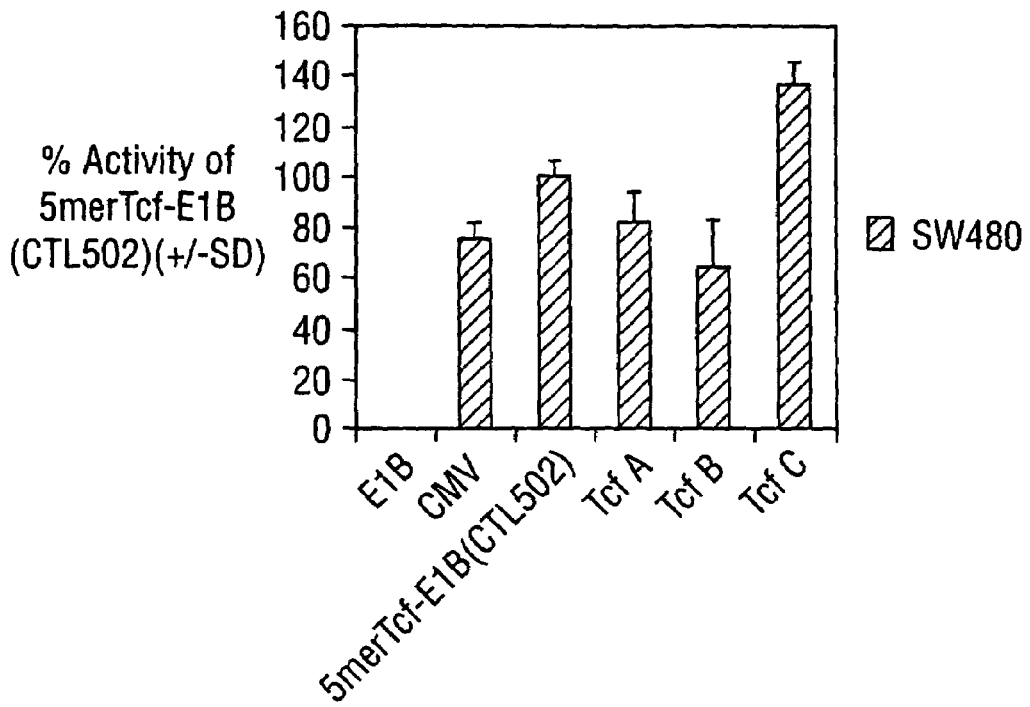
Figure 8B:
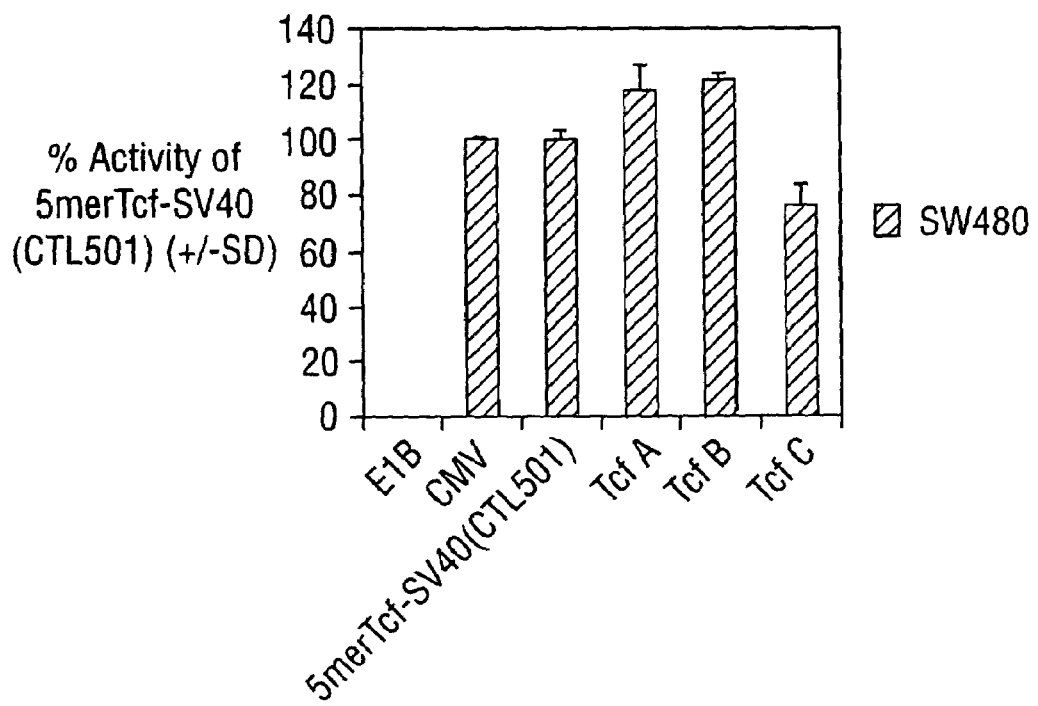

FIGS. 8*a-b* show the results of transient transfections of SW480 cells using the indicated Tcf responsive luciferase reporter constructs. TcfA, TcfB and TcfC were either combined with the minimal adenoviral E1BTATA box or with the SV40 basal promoter (see FIG. 7 for a description of TcfA, TcfB and TcfC). The E1B, 5merTcf-SV40 (CTL501), 5merTcf-E1BTATA (CTL502) and CMV reporter plasmids are described in the legend to FIG. 6. Cells were transfected with equimolar amounts (about 0.5 µg each) of each luciferase reporter constructs. Data are expressed as percentage activity of 5merTcf-E1BTATA (CTL502) (a) or 5merTcf-SV40 (CTL501) (b), respectively. The mean value and SD of triplicate transfections are shown. These data are representative of three independent experiments.

Figure 9A:
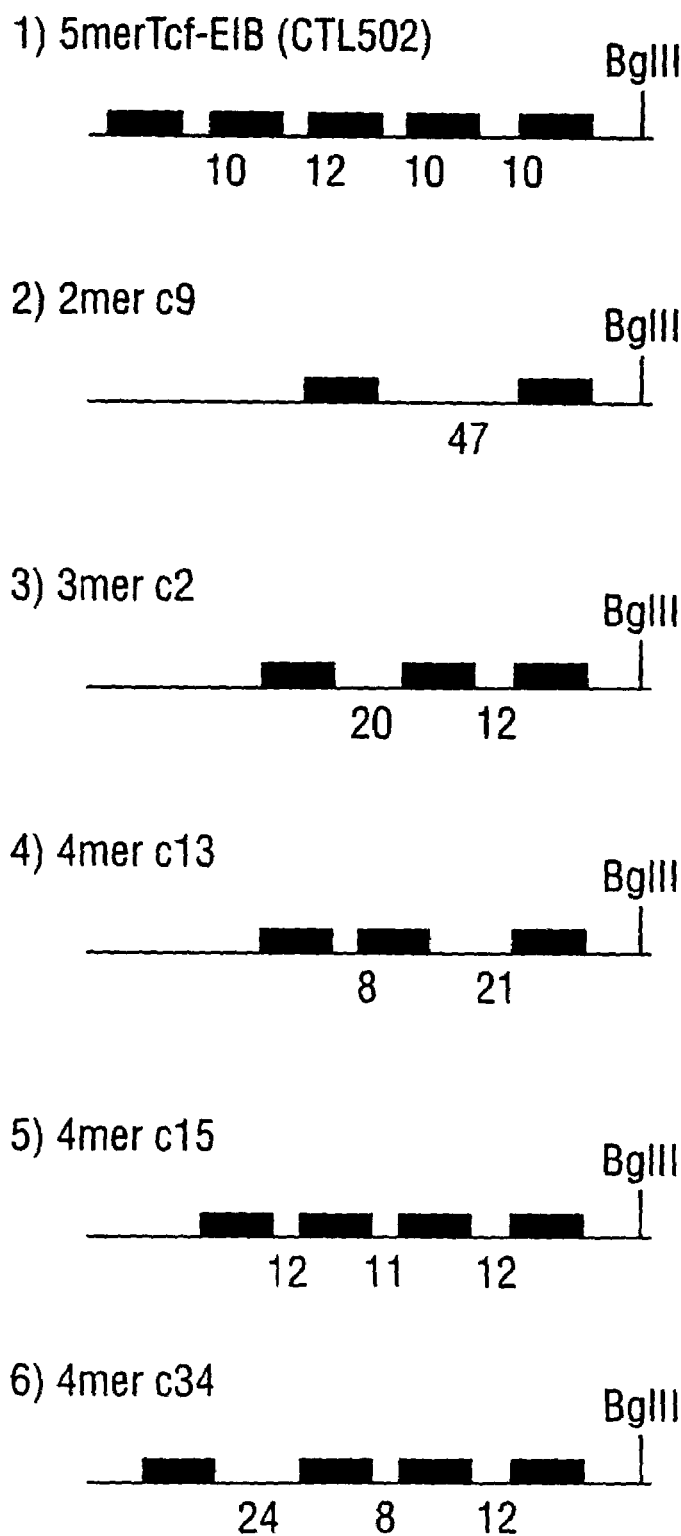
Figure 9B:
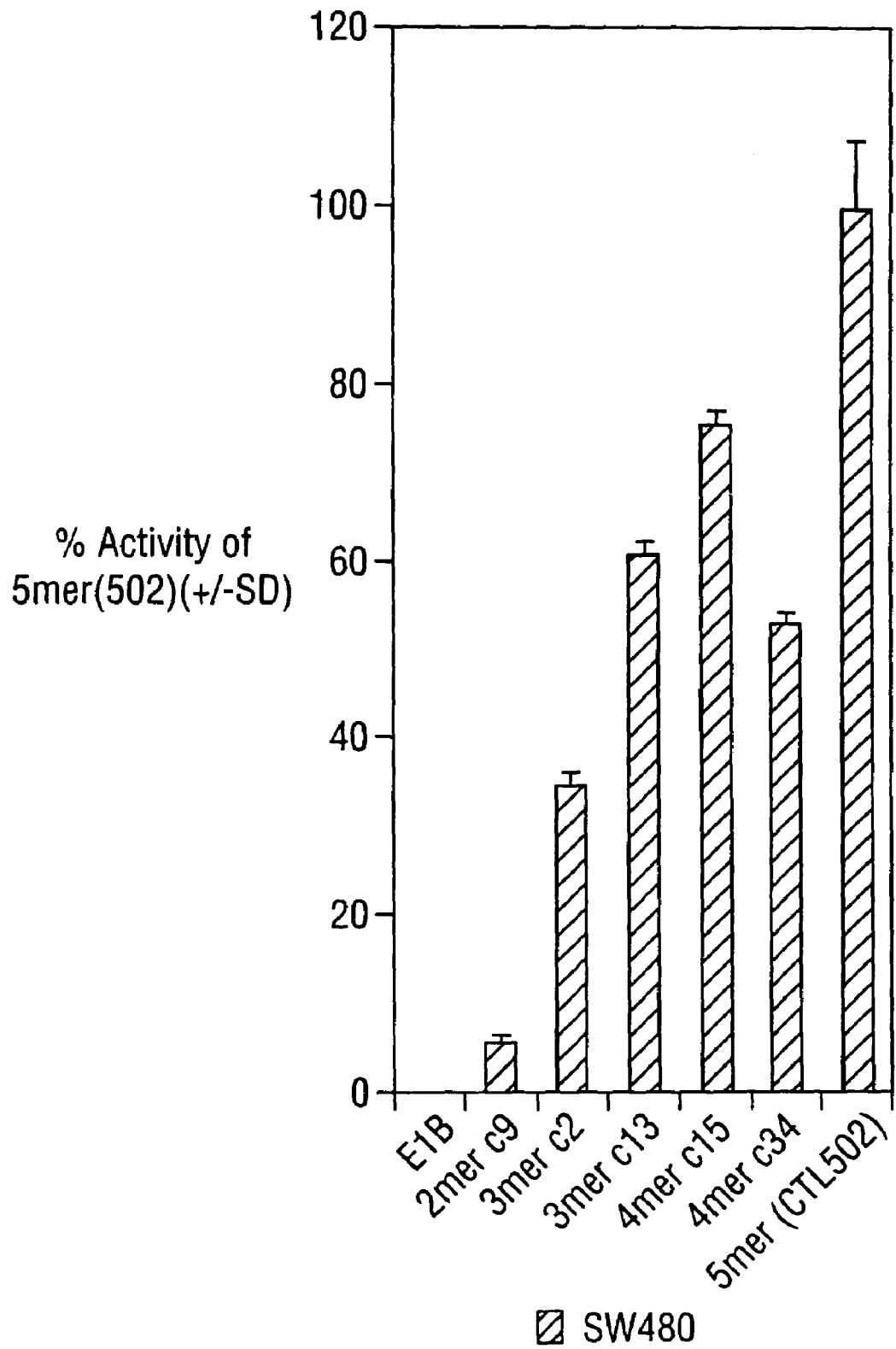

FIGS. 9*a-c* shows the results of transient transfections of SW480 cells using Tcf-E1BTATA luciferase reporter constructs with different numbers and arrangements of Tcf binding sites. FIG. 9*a* shows the number of Tcf sites and the spacing between them. FIG. 9*c* shows the nucleotide sequence of the antisense strands of the Tcf-E1BTATA constructs (SEQ ID NOs: 22, 23, 24, 25, and 26). The sequences underlined and in italics are active Tcf sites. The sequences in bold are the Bg/II, NheI and KpnI recognition sites. In the 4merTcf-E1BTATA construct the Bg/II site is defective. Cells were transfected with 0.5 µg of each luciferase reporter construct. Data are expressed as percent-age activity of 5merTcf-E1BTATA (CTL502) (FIG. 9*b*). The mean value and SD of triplicate transfections are shown. The results are representative of three independent experiments.

FIGS. 10*a-c* shows the results of transient transfections of SW480 cells with TcfC-E1BTATA-luc constructs with variable spacing between the proximal Tcf site and the TATA box (25–499 bp). The structure of the TcfC element is described in FIG. 7. FIG. 10*a* shows the structure of the TcfC-E1BTATA reporter constructs used for this assay. "d" indicates the number of base pairs from the last nucleotide of the proximal Tcf binding site to the first T of the TATA sequence. The 88 bp and 447 bp spacer fragments were derived by PCR from the human β-globin gene intron II. Cells were transfected with 0.5 µg of each luciferase reporter construct. Data are expressed as percentage activity of the TcfC-E1BTATA d=25 construct (b). The mean value and SD of triplicate transfections are shown. The results are representative of three independent experiments. The nucleotide sequence of the antisense strand of TcfC-E1BTATA when d=25 (SEQ ID NO: 27) is shown in FIG. 10*c*. The sequences underlined and in italics are active Tcf sites. The sequences in bold are the E1B TATA box, and the SmaI and KpnI recognition sites.

FIG. 11 shows the quantitation by ELISA of NTR expressed by HeLa and SW480 cells infected with CTL102, CTL501 and CTL502. Cells were infected with a range of mois (1, 5, 20, 100, 500 and 1500 pfu/cell). Cytoplasmic extracts were prepared two days later and assayed for NTR by ELISA (materials and methods). Mean values of duplicate infections are shown.

Figure 12A:
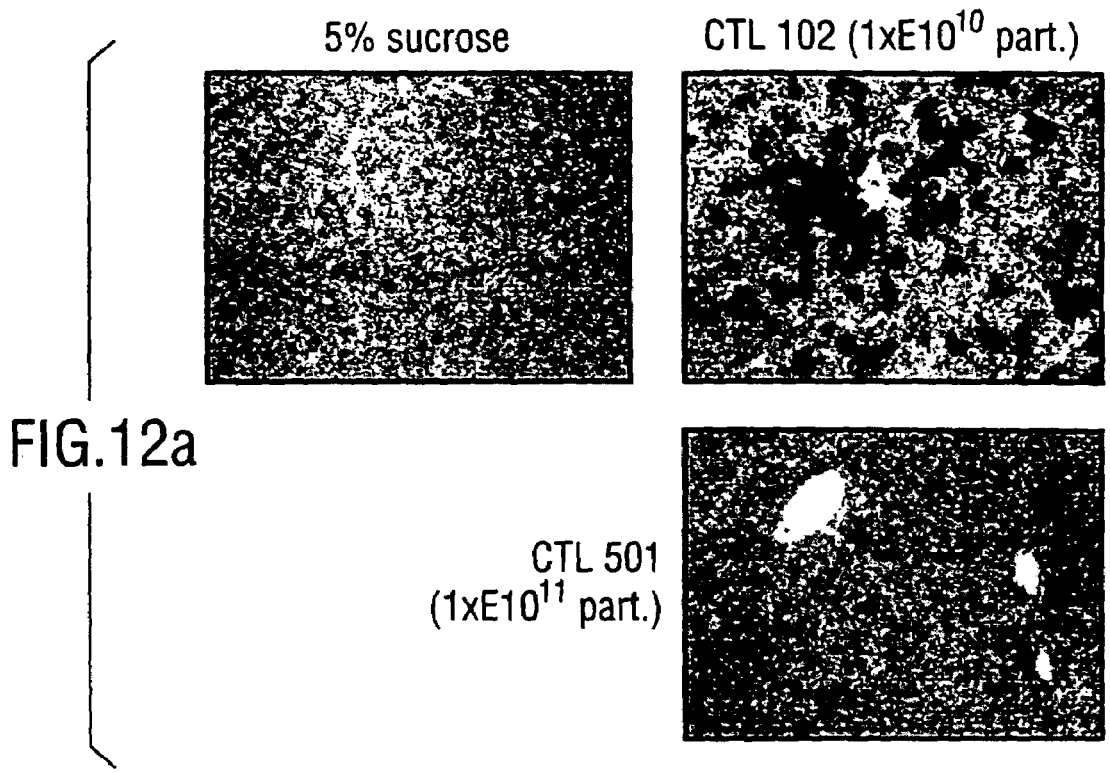
Figure 12B:
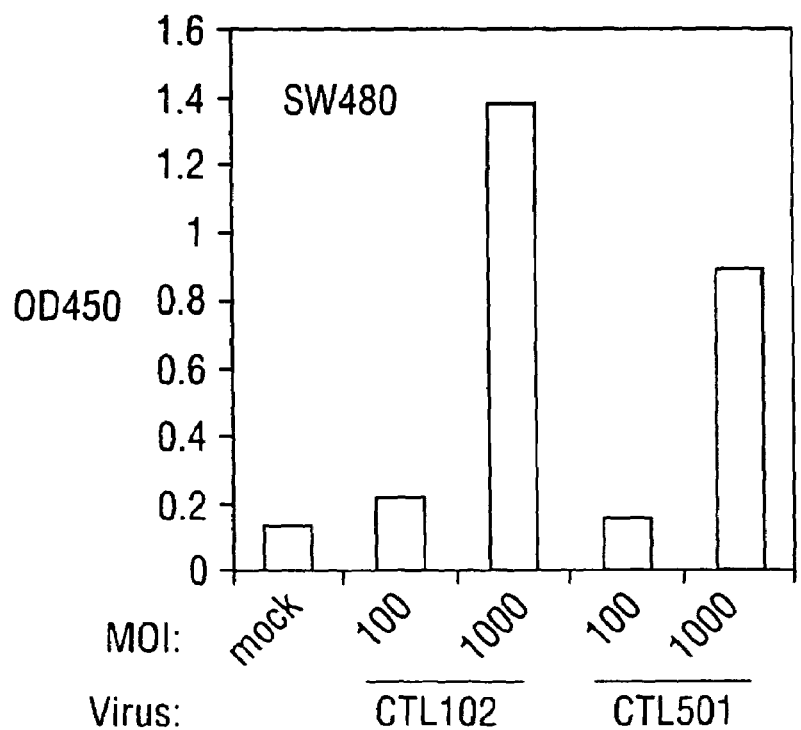

FIGS. 12*a-b* show a comparison of the levels of recombinant adenovirus-directed NTR expression in the livers of normal mice following i.v. injection with CTL102 and CTL501. Mice were tail vein injected with the indicated quantities of CTL102 or CTL501, sacrificed 48 h later and livers stained for NTR as described in Materials and methods for tumour sections.

Figure 13:
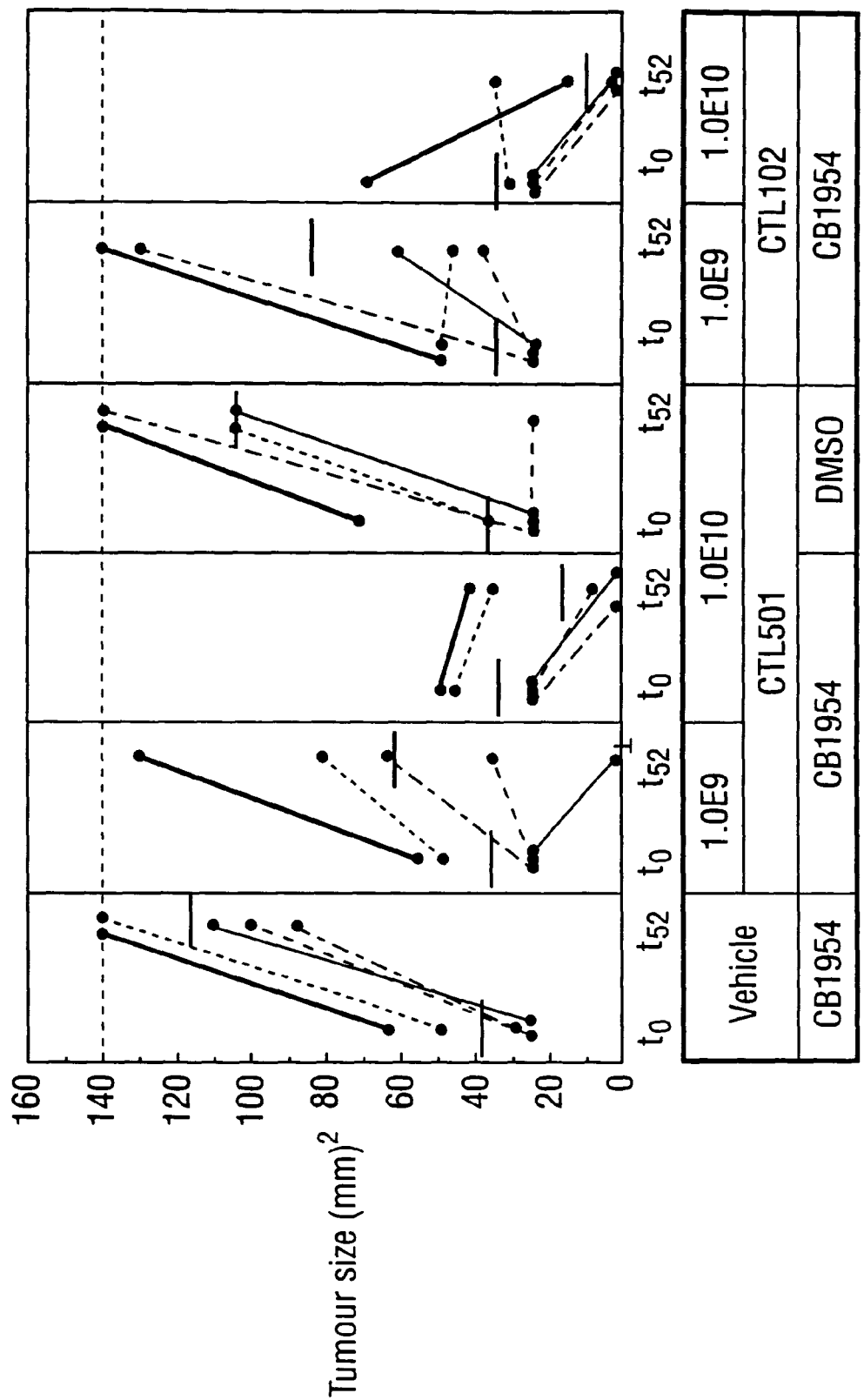

FIG. 13 shows a comparison of the level of anti-tumour efficacy of CTL501/CB1954 with CTL102/CB1954 in a xenograft model of colon cancer. Groups of SW480 tumours (n=5) ranging in size from 20–80 mm$^2$ cross sectional area were injected with a single dose ($10^9$ or $10^{10}$ particles) of either CTL102 or CTL501. Prodrug treatment and tumour measurement were done as described in Materials and methods.

Figure 14:
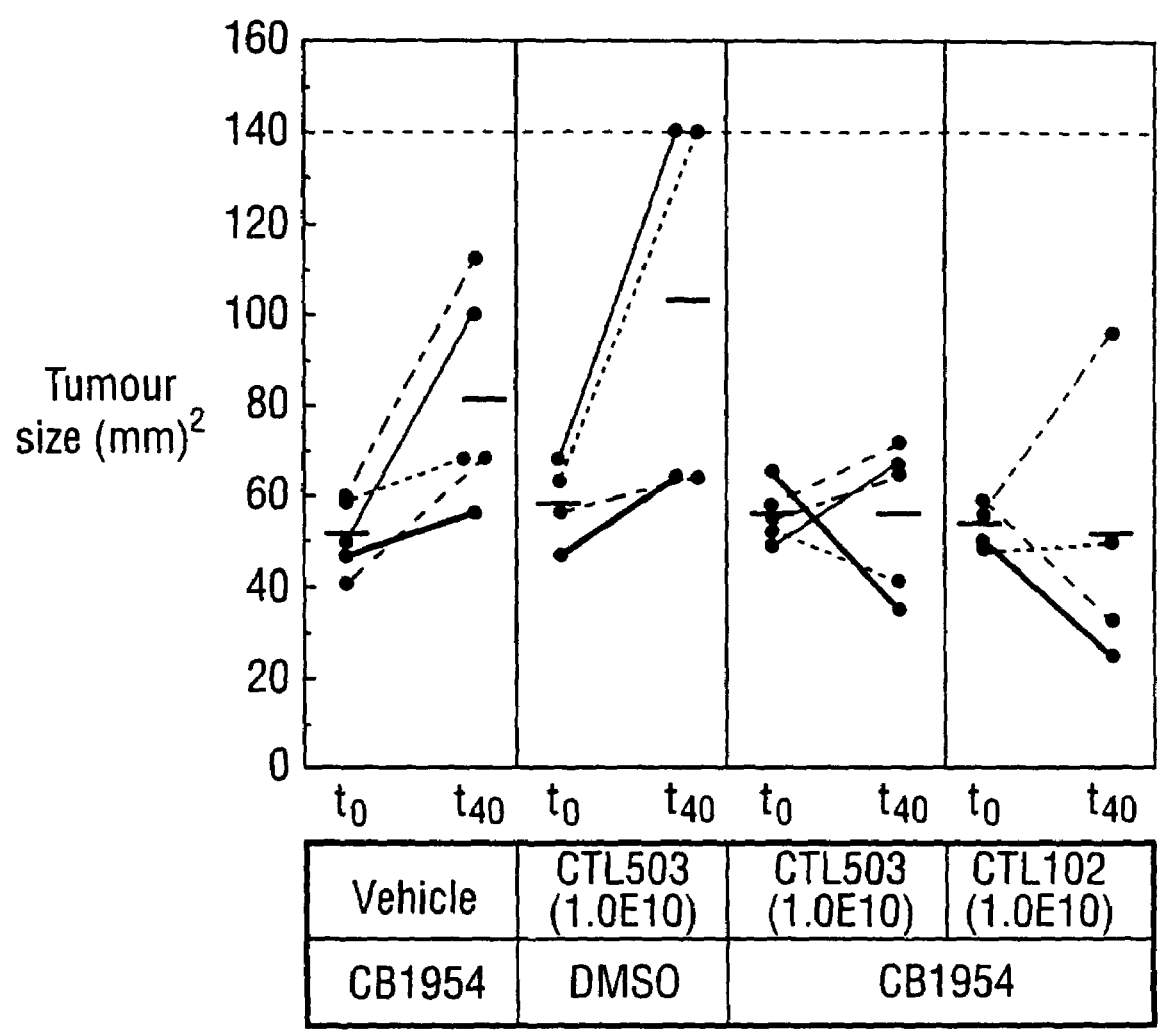

FIG. 14 shows a comparison of the level of anti-tumour efficacy of CTL503/CB1954 with CTL102/CB1954 in a xenograft model of colon cancer. Groups of SW480 tumours (n=5) ranging in size from 20–80 mm$^2$ cross sectional area were injected with a single dose ($10^{10}$ particles) of either CTL102 or CTL503. Prodrug treatment and tumour measurement were done as described in Materials and methods.

FIGS. 15*a-d* show that CTP1 and CTP3 express at very low levels in normal human endothelial cells, dermal fibroblasts and hepatocytes. Cells were infected with Ad.CMV-nLacZ, Ad.CTP1-nLacZ and Ad.CTP3-nLacZ as described in Materials and methods and analysed 48 h later. For the data shown in FIGS. 15*a* and *b*, extracts were prepared from cells infected with the indicated MOIs (pfu/cell) and beta-galactosidase assayed using the Galacto-Light assay system as described by the supplier. Error bars represent standard deviation. A representative experiment is shown in each case. In FIG. 15c, cells were infected with an MOI of 1000 pfu/cell and beta-galactosidase-expressing cells visualised by X-Gal staining. Only fibroblasts infected with Ad.CMV-nLacZ expressed detectable enzyme. FIG. 15d shows that all three viruses directed high-level beta-galactosidase expression in infected SW480 colon cancer cells.

FIGS. 16a–b show that CTP1 and CTP3 express at very low levels under replicating conditions in the adenovirus helper cell lines (PerC6 and 293). PerC6 and 293 cells were infected at an MOI Of 100 and harvested 30 h later. Cell extracts were then prepared and assayed for β-galactosidase as described in Materials and methods. Error bars represent standard deviation. A representative experiment is shown. FIG. 16a has a logarithmic, and 16b a linear, scale.

FIG. 17 shows that CTP1 and CTP3 express at high levels in secondary colorectal cancer tissue but not in attached liver tissue. 2–3 mm³ segments of freshly excised secondary colorectal cancer (liver) with attached liver margin tissue were incubated in the indicated viruses, fixed 48 h later and stained for β-galactosidase expression as described in Materials and methods. "T" denotes tumour tissue, "L" denotes attached liver tissue.

FIGS. 18a–b shows that high-level CTP1 and CTP3 expression in primary colorectal cancer specimens correlates with high-level, non-membranous expression of β-catenin.

2–3 mm³ segments of freshly excised primary colorectal cancer were transduced with the indicated viruses and stained for β-galactosidase expression as described in Materials and methods. Samples of each tumour were sectioned and stained for β-catenin expression as described in Materials and Methods.

DETAILED DESCRIPTION OF THE INVENTION

The invention is described in detail by the use of the following examples. These are by way of illustration only and are not to be taken as limiting.

EXAMPLES

Materials and Methods

Cell Culture

HepG2 (human liver carcinoma; mutated β-catenin), SW480 (human colon carcinoma, mutated APC) and HeLa (human cervix carcinoma) cell lines were obtained from ATCC and were maintained as recommended by the supplier. PER.C6 (human embryonic retinoblast cell line) cells were obtained from IntroGene, (Fallaux et al., Human Gene Ther., 9: 1909–1917, 1998) and were cultured in DMEM supplemented with 10% FCS, 2 mM $MgCl_2$ and antibiotics (150 μg/ml penicillin, 250 μg/ml streptomycin).

Primary human dermal fibroblasts were isolated from punch biopsy samples from healthy volunteers and maintained as above. HUVEC cells were obtained from Promocell (Heidelberg, Germany) and maintained in Endothelial Growth Medium plus Supplement Mix (Promocell). Primary hepatocytes were maintained in Williams medium with added antibiotics, glutamine, insulin and hydrocortisone.

Plasmid Construction

To clone pGL3pro/5merTcf-SV40 (CTL501) two partially double-stranded fragments were generated by annealing the partly complementary pairs of oligonucleotides 1 with 2, and 3 with 4.

```
Oligo 1: PCT AGC AAG CTT ACT AGT CCT TTG ATC AAG AGT CCT ACC    (SEQ ID NO:1)
         TTT GAT CTC TAA ATG CAC CTT TGA TC Oligo 2: PAC TGA ATT CCT TGA TCA AAG GTG CAT TTA GAG ATC AAA    (SEQ ID NO:2)
         GGT AGG ACT CTT GAT CAA AGG ACT AGT AAG CTT G Oligo 3: PAA GGA ATT CAG TCC TTT GAT CAA GAG TCC TAC CTT TGA    (SEQ ID NO:3)
         TCT CTA AAT GCA CCT TTG ATC A Oligo 4: PGA TCT GAT CAA AGG TGC ATT TAG AGA TCA AAG GTA GGA    (SEQ ID NO:4)
         CTC TTG ATC AAA GG
```

(where P indicates phosphate modification)

These fragments each contain three TCF binding sites (consensus CCTTTGATC). These two double-stranded fragments were ligated and the resulting fragment (about 130 bp) containing six TCF sites was cloned by their NheI and Bg/II sites into NheI/Bg/II-digested pGL3 promoter plasmid (pGL3pro; Promega) resulting in pGL3pro/5merTcf-SV40 clone 10. However, sequencing revealed that the most 3' TCF-binding site contained a deletion of one G nucleotide, producing an inactive site (CCTTTATC) (See FIG. 1c).

To generate pGL3basic/5merTcf-E1BTATA (CTL502) 84 bp from the Clontech plasmid pG5CAT, spanning 21 bp upstream and 55 bp downstream of the adenoviral E1BTATA box (TATATAAT), were amplified with PCR using oligos containing Bg/II and HindIII overhangs. This fragment, containing 16 bp of the Ad5 E1B promoter (GGG-TATATAATGCGCC) (SEQ ID NO:11), was then cloned into Bg/II/HindIII-digested pGL3basic resulting in pGL3basic/E1BTATA clone 2 (see FIG. 6c). Then the 5-mer TCF sites from pGL3basic/5merTcf-SV40 (CTL501) clone 10 were cut out by NheI/Bg/II digestion and cloned into NheI/Bg/II-digested pGL3basic/E1BTATA clone 2, resulting in pGL3basic/5merTcf-E1BTATA clone 1. Sequencing confirmed the expected construct.

To generate pGL3pro/TcfA-SV40 clone 4, pGL3pro/TcfB-SV40 clone 31, pGL3pro/TcfC-SV40 clone 3, pGL3basic/TcfA-E1BTATA clone 28, pGL3basic/TcfB-E1BTATA clone 10 and pGL3basic/TcfC-E1BTATA clone 1, oligonucleotides 5, 7 and 9, respectively, each containing 5 active TCF binding sites (CCTTTGATC) and an intentionally mutated site (CCTTTATC, for consistency) were annealed to their respective antisense oligonucleotides, 6, 8 and 10.

```
Oligo 5:  CTA GCA AGC TTA CTA GTC CTT TGA TCA AGA GTT TCC TAC      (SEQ ID NO:5)

CTT TGA TCT CTA AAT TGC ACC TTT GAT CAA GGA ATT CAG TCC TTT

GAT CAA GAG TAA CCT ACC TTT GAT CTC TAA ATG CAC CTT TAT CA

Oligo 6:  GAT CTG ATA AAG GTG CAT TTA GAG ATC AAA GGT AGG TTA       (SEQ ID NO:6)

CTC TTG ATC AAA GGA CTG AAT TCC TTG ATC AAA GGT GCA ATT TAG

AGA TCA AAG GTA GGA AAC TCT TGA TCA AAG GAC TAG TAA GCT TG

Oligo 7:  CTA GCA AGC TTA CTA GTC CTT TGA TCA AGC TAC CTT TGA       (SEQ ID NO:7)

TCT CTA GCA CCT TTG ATC AAG AGT CCT TTG ATC AAG CCT ACC TTT

GAT CTC TAA ATG CAC CTT TAT CA

Oligo 8:  GAT CTG ATA AAG GTG CAT TTA GAG ATC AAA GGT AGG CTT       (SEQ ID NO:8)

GAT CAA AGG ACT CTT GAT CAA AGG TGC TAG AGA TCA AAG GTA GCT

TGA TCA AGA GAC TAG TAA GCT TG

Oligo 9:  CTA GCA AGC TTA CTA GTC CTT TGA TCA ATA CCT TTG ATC       (SEQ ID NO:9)

TCA CCT TTG ATC AAG TCC TTT GAT CAT ACC TTT GAT CTC TAA ATG

CAC CTT TAT CA

Oligo 10: GAT CTG ATA AAG GTG CAT TTA GAG ATC AAA GGT ATG ATC       (SEQ ID NO:10)

AAA GGA CTT GAT CAA AGG TGA GAT CAA AGG TAT TGA TCA AAG GAC

TAG TAA GCT TG (all six oligonucleotides were modified by 5' phosphate).
```

The resulting fragments containing NheI/Bg/II overhangs were cloned into NheI/Bg/II digested pGL3promoter or NheI/Bg/II digested pGL3basic/E1BTATA clone 2 to generate the aforementioned constructs. The sequences were confirmed to be as expected.

The constructs pGL3basic/2merTcf-E1BTATA clone 9, pGL3basic/3merTcf-E1BTATA clone 2, pGL3basic/3merTcf-E1BTATA clone 13, pGL3basic/4merTcf-E1BTATA clone 15 and pGL3basic/4merTcf-E1BTATA clone 34 were cloned by the same way, but, these constructs have one or more Tcf sites deleted most probably due to loop generation during annealing and following excision of loops in E. coli after transformation. For spacing between the TCF sites and confirmed sequences for these constructs see FIGS. 9a and c.

pGL3basic/88-E1BTATA clone 8 and pGL3basic/TcfC-88-E1BTATA clone 2 (distance to TATA box: d=140) were constructed by cloning a PCR amplified 88 bp fragment (5' oligo: GAAGATCTCCCCTTCTTTTCTATGGTTAAG (SEQ ID NO:12), 3' oligo: GAAGATCTGCAATCAT-TCGTCTGTTTCCC) (SEQ ID NO:13) from the human β-globin gene intron 11 using Bg/II overhangs into Bg/II-digested pGL3basic/E1BTATA clone 2 or Bg/II digested pGL3basic/TcfC-E1BTATA clone 1, respectively.

pGL3basic/447-E1BTATA clone 1 and pGL3basic/TcfC-447-E1BTATA clone 6 (distance to TATA box: d=499) were cloned by inserting a PCR amplified 447 bp fragment (5' oligo: GAAGATCTCCCCTTCTTTTCTATGGTTAAG (SEQ ID NO:12), 3' oligo: GAAGATCTGATTTGG TCAATATGTGTACAC) (SEQ ID NO:14) from the human β-globin gene intron II using Bg/II overhangs into Bg/II-digested pGL3basic/E1BTATA clone 2 or Bg/II-digested pGL3basic/TcfC-E1BTATA clone 1. The sequences were confirmed.

To create pGL3basic/TcfC-25-E1BTATA clone 6 (distance to TATA box: d=25), the TcfC fragment was cut out by HindIII/Bg/II digest from pGL3basic/TcfC-E1BTATA clone 1 and then blunted with mung bean nuclease (NEB). The blunted fragment was cloned into a partially XbaI-digested, mung bean nuclease-blunted pGL3basic/E1BTATA clone 2, to create the intermediate construct pGL3basic/TcfC-25-E1BTATA clone 19. From here, we had to reclone the TcfC-25-E1BTATA promoter fragment into pGL3basic as the plasmid backbone immediately upstream of the promoter was changed for unknown reasons in clone 19. Therefore the TcfC-25-E1BTATA promoter was cut out by SpeI/HindIII digest from pGL3basic/TcfC-25-E1BTATA clone 19 and then blunted with Klenow enzyme. Finally, the blunted TcfC-25-E1BTATA fragment was cloned into HindIII digested and Klenow-blunted pGL3basic to generate pGL3basic/TcfC-25-E1BTATA clone 6 (d=25) with the correct plasmid backbone. The sequence was determined since the blunting process is error-prone (see FIG. 10c)

Transient Transfections and Luciferase Assay

HepG2, SW480 and HeLa were seeded the day before transfection at densities of $2.5 \times 10^5$, $1.5 \times 10^5$ and $6.0 \times 10^4$ cells per 6-well respectively. The next day, a mixture of CL22 peptide (KKKKKKGGFLGFWRGENGRKTRSAY-ERMCNILKGK (SEQ ID NO:15) (described in International Patent Application WO 98/35984)) and plasmid DNA (2:1 ratio, µg:µg) was prepared in a final volume of 100 µl in HBS (10 mM Hepes pH 7.4, 150 mM NaCl; Sigma) and incubated at RT for 30–45 min before addition of 0.9 ml of "RAC" solution (0.1% human albumin (BPL, UK), 120 µM chloroquine (Sigma) in RPMI medium (Sigma). The transfection solution was then added to cells after washing them once with PBS and incubated with the cells for 4–5 hours before replacement with 2 ml of fresh complete medium. After two days, cells were washed once with PBS and then incubated for 10 min at RT in 200 µl lysis buffer (10 mM sodium phosphate pH 7.8, 8 mM $MgCl_2$, 1 mM EDTA pH 8.0, 1% Triton X-100 and 15% glycerol). After centrifugation, an aliquot of the supernatant was assayed for luciferase activity with luciferase assay buffer (0.1 mM luciferin, 0.44 mM ATP in lysis buffer) using a luminometer (Lumat LB 9501, Berthold, Germany). Activity was normalised using the protein content of each sample (BCA, Pierce).

Construction of Replication Defective Adenoviruses Expressing NTR

The transfer vectors used to construct the recombinant adenoviruses c1/CTL501, c13 and CTL502 i.e. pPS1128/5merTcf-SV40 (clones 1 and 13) and pPS1128/5merTcf-E1BTATA (clone 10) respectively were constructed in two stages. In the first, the 5merTcf-SV40 promoter from pGL3pro/5merTcf-SV40 clone 10 and the 5merTcf-E1BTATA promoter from pGL3basic/5merTcf-E1BTATA clone 1 were cloned as Hind III fragments into HindIII digested pTX0374 resulting in replacement of the CMV enhancer/promoter with the respective Tcf promoters to create "pTX0374/5merTcf-SV40 clone 8" and "pTX0374/5merTcf-E1BTATA clone 1". pTX0374 contains a CMV-NTR-IVSII-p(A) (NTR: E. coli B/r nitroreductase gene amplified from genomic DNA) expression cassette with the human β-globin intron II for transcriptional stabilisation and the Complement 2 gene poly(A) signal for termination and the plasmid pBluescript KS+ as backbone. In the second stage, the complete expression cassettes from pTX0374/5merTcf-SV40 clone 8 and pTX0374/5merTcf-E1BTATA clone 1 were recloned into SpeI digested pPS1128 to create "pPS1128/5merTcf-SV40 clones 1 and 13" (clone 1: left to right orientation in E1; clone 13: right to left orientation in E1) and "pPS1128/5merTcf-E1BTATA clone 10 (left to right orientation in E1). pPS1128 was kindly provided by Dr. P. Searle, CRC Institute of Cancer Studies, University of Birmingham. pPS1128 contains adenoviral sequences from the left hand ITR to nt 359 and from nt 3525 to 10,589 and is therefore an E1-deleted vector.

pTX0375, the transfer vector used to generate CTL102, was constructed by cloning a SpeI fragment spanning the whole expression cassette (CMT-NTR-IVSII-p(A)) from pTX0374 into SpeI digested pPS1128 and identification of a clone containing the cassette in the left to right orientation.

The adenoviral "backbone" vector pPS1160 was constructed by PacI linearisation of pPS1128, ligation with a PacI-compatible adaptor (oligo1: 5'-TACATCTAGATAAT (SEQ ID NO:16)-3', oligo2: 5'-TTATCTAGATGTA (SEQ ID NO:17)-3') containing an XbaI site followed by XbaI digestion to release a ca. 7 kb XbaI fragment containing Ad5 sequences 3524–10589. This was then cloned into XbaI linearised pPS1022 (Dr. Peter Searle) a pUC18-based plasmid containing Ad5 sequences from nt 10,589 to the right hand ITR but lacking nt 28,592 to 30,470 (E3 region).

The recombinant viruses CTL501, CTL502 and CTL102 were constructed by homologous recombination in Per.C6 cells. These were cotransfected with an equimolar mixture of pPS1128/5merTcf-SV40 (clone 1 or clone 13), pPS1128/5merTcf-E1BTATA (clone 10) or pTX0375, respectively, and pPS1160 into 90% confluent PER.C6 cells. The recombinant viruses were harvested about 7 days later by 3 freeze-thaw cycles in infection medium (DMEM, 1% FCS, 2 mM $MgCl_2$). By repeated infection/harvesting cycles the viruses were grown to large scale and then purified by standard CsCl density centrifugation, dialysed against excess of storage buffer (10 mM Tris pH 7.4, 140 mM NaCl, 5 mM KCl, 0.6 mM $Na_2HPO_4$, 0.9 mM $CaCl_2$, 0.5 mM $MgCl_2$ and 5% sucrose) and finally snap-frozen in liquid nitrogen and stored at −80° C. Particle concentrations were determined using the BCA Protein Assay Reagent (Pierce). Infectious titres were either estimated on the assumption that 1 in 100 particles are infectious or were determined in a limiting dilution standard method against a defined internal virus standard. Adenoviral DNA was characterised by restriction digestion and direct sequencing using viral DNA as a template (the promoter region up to the starting NTR reading frame was sequenced).

pTX0374 was constructed by cloning a 1.6 kb Bg/II-BamHI fragment containing the CMV promoter fused to the E. coli ntr gene into pSW107. This plasmid was constructed by cloning a 917 bp fragment of the human beta-globin gene (BamHI site in exon2 to the EcoRI site in exon3) coupled to a 240 bp HincII-BamHI fragment containing the polyA addition and transcriptional termination signals of the human complement C2 gene into pBluescript (Stratagene). pTX0375 was constructed by cloning a 2.5 kb SpeI fragment from pTX0374 into SpeI-digested pPS1128. This plasmid was constructed in two stages. In the first, the left hand EcoRI site of pPS971 (Weedon et al, Int. J. Cancer, in press) was converted to a SwaI site to create pPS115. In the second, the 350 bp Spe1-AflII fragment of pPS115 was replaced with a linker prepared by annealing the two oligonucleotides:

(SEQ ID NO:18)
5'-CTAGTATCGATTGTTAATTAAGGGCGTGGCC-3' and (SEQ ID NO:19)
5'-TTAAGGCCACGCCCTTAATTAACAATCGATA-3'.

pPS1022 was constructed from pPS972 by conversion of the right hand EcoRI site to a SwaI site.

It will be appreciated by those skilled in the art that any suitable vector may be used in the construction of the Tcf responsive element of the present invention. In particular, it will be appreciated that any suitable adenovirus based vector can be used in the construction of the Tcf responsive element of the present invention.

Preparation of Adenoviral DNA

Viral DNA was prepared from about $10^{11}$ CsCl-banded virus particles by incubation with 100 µg/ml proteinase K in 20 mM Tris/HCl pH 7.5, 5 mM EDTA pH 8.0, 0.1% SDS for 3–4 hours at 37° C. The crude DNA preparation was then extracted two times with an equal volume of Phenol:Chloroform:Isoamylalcohol (25:24:1), once with chloroform only and then precipitated with 1/10 Vol. 3.0 M Na Acetate and 2 Vol. 100% Ethanol in a dry ice/ethanol bath for 10 min. After centrifugation, (10 min at 13K at RT) the resultant DNA pellet was washed with 70% Ethanol, air-dried and then resuspended in water. Viral DNA was analysed by restriction digestion. The promoter regions of CTL501 and CTL502 were analysed by DNA sequencing (Seqlab GmbH, Germany).

Assay of NTR Expressed by Virus Transduced Cells (ELISA)

1–1.5×$10^4$ cells per 6-well cell culture plate were transduced by incubation with virus in infection medium (DMEM/1% FCS) for 90 min at 37° C. in a 5% $CO_2$ atmosphere followed by incubation in complete medium for 2 days.

Cytoplasmic extracts were then prepared by hypotonic lysis. Cells were washed with PBS before lysis with ice-cold hypotonic lysis buffer (10 mM Tris pH 7.5) for 45 min on ice. Extracts were cleared by centrifugation at 13K for 2 min. 96-wells (Nunc-Immuno Plate Maxisorp Assay Plates) were coated overnight in triplicate with 50 µl extract. Wells were washed three times with PBS/0.5% Tween20 and then incubated with sheep anti-NTR polyclonal antibody (100 µl of 1:2,000 dilution in PBS/0.5% Tween20) for 30 min at RT. After removal of excess primary antiserum by washing 3× with PBS/0.5% Tween20 the extracts were incubated with donkey anti-sheep HRP conjugate (100 µl of 1:5,000 dilution in PBS/0.5% Tween20) for 30 min at RT. After three washes with PBS wells were incubated with 100 µl of a solution prepared by mixing 1 ml of TMB (1 mg/ml in DMSO; Sigma) with 9 ml 0.05 M phosphate-citrate buffer (Sigma) and 2 µl of 30% (v/v) $H_2O_2$. Wells were incubated for 15 min at RT and the reaction stopped with 25 µl of 2M $H_2SO_4$. OD 450 nm was read using a 96-well plate reader (Labsystems Multiscan MS).

NTR Immunostaining of Virus-injected Xenografts

SW480 tumours were injected with 20 µl of either CTL102 or CTL501 and excised 48 hours later following humane sacrifice. The tumours were then fixed in 4% formalin/PBS for 20–24 hours at 4° C. before embedding in paraffin wax (Citadel 2000). 3–4 µm wax sections were cut and collected on APES-treated glass slides. Sections were dewaxed, rehydrated and washed 2× in PBS/0.01% Tween20 (5 min) and then immersed in 0.25% $H_2O_2$/PBS for 30 min at RT. Sections were then washed 3× in PBS/0.01% Tween20 (5 min) and then permeabilised with ice cold 0.1% Triton-X100 for 5 min at RT followed by 2× washing for 5 min in PBS/0.01% Tween200. Sections were then blocked with 5% normal rabbit serum in PBS for 60 min at RT before incubation with a polyclonal sheep anti-NTR (1:2,000 diluted in PBS) for 60 min at RT. Excess primary antibody was removed by washing 3× with PBS/0.01% Tween20 (5 min) before incubation with a biotinylated anti-sheep IgG/Streptavidin-HRP solution (Vectastain ABC kit, Vector Laboratories, PK-6106, 1:200 diluted in PBS) for 30 min at RT.

Sections were washed 3× for 5 min with PBS/0.01% Tween20 and then incubated with freshly prepared AEC reagent (Vectastain, Vector Laboratories). Reactions were stopped after 10 min by washing in water and finally sections were mounted in an aqueous mountant. Staining was analysed by counting the number of positively stained cells within a standardised area.

Generation of Subcutaneous Tumour Xenografts in Nude Mice

Tumour xenografts were generated by subcutaneous injection of one flank of male Balb/c nu/nu mice (6–8 weeks old, Harlan UK) with 100 µl of a suspension of exponentially growing cultured tumour cells, washed and resuspended in sterile saline solution. Cell viability was at least 90%. For HepG2 an innoculum of $5 \times 10^6$ cells was used. For SW480 this was slightly lower at $2 \times 10^6$ cells. Following injection, mice were kept in a sterile environment and examined regularly for the appearance of tumour xenografts.

Intratumoural Injection of CTL102 and CTL501

A U-100 insulin syringe (TERUMO, Leuven, Belgium) fitted with a fixed 27-gauge needle was used to inject 20 µl of virus suspension or vehicle alone (5% sucrose in 25 mM Tris-HCl, pH 7.4) directly into tumours through the skin. To avoid virus leakage, injections were performed in a continuous slow movement and the needle was held in place for about 15 seconds after injection was completed.

CB1954 Treatment Schedule and Tumour Size Measurements

CB1954, freshly dissolved in DMSO and diluted 1 in 5 with NSS, was administered by intraperitoneal injection. Mice received 5 consecutive daily doses of 20 mg/kg body weight. Mice treated with the vehicle alone were injected with 20% DMSO/saline (5.0 µl/kg body weight). Tumour growth was monitored by measuring the tumour diameter through the skin in two perpendicular dimensions (length and width) using callipers and expressed as surface area (length×width=$mm^2$). To prevent undue suffering compulsory sacrifice was carried out when the tumour reached 140 $mm^2$. Weight loss and changes in animal behaviour (signs of distress) were also recorded.

Intravenous Injection of CTL501/CTL102 and CB1954 Administration in Nude Mice

A syringe fitted with a fixed 27-gauge needle was used to administer 100 µl of virus suspension into the tail vein of nude mice. After 48 hours, CB1954 was administered as described above. Mice were monitored and weighed daily. To prevent undue suffering to animals humane sacrifice was carried out if mouse body weight was reduced by more than 20% or at the onset of any sign of severe distress.

Ex Vivo Transduction of Freshly Excised Colorectal Tumour Samples

Freshly excised tumour tissue was extensively washed (at least 10 minutes duration) under aseptic conditions with 20 ml of Earl's MEM containing 10% FCS, 150 µg/ml penicillin, 250 µg/ml streptomycin, 10 µg/ml tetracycline, 100 µg/ml amikacin, 150 g/ml chloramphenicol and 100 µg/ml gentamycin and stored at 4° C. overnight in medium containing 10% FCS. After removal of fat and grossly and suspected necrotic tissue, 2–3 $mm^3$ samples were prepared and placed individually into wells of a 96-well plate. Samples (in quadruplicate) were incubated in 150 µl of serum-free medium containing, $1.0 \times 10^{10}$ virus particles or in medium alone for 4 h in a $CO_2$ incubator. The medium was then replaced with EMEM containing 10% FCS and the samples incubated for a further 44 h to allow gene expression to proceed. β-galactosidase expression was visualised after fixation of the tumour samples in 2% paraformaldehyde/PBS for 2 h at 4° C. and washing with PBS by overnight incubation in X-gal staining solution at 37° C.

β-Catenin Immunohistochemical Staining

Paraffin-embedded sections were stained for β-catenin using rabbit polyclonal antiserum (Santa Cruz Biotechnology Inc) and vector AEC kit.

Construction of CTL503, Ad.CTP1-nLacZ and Ad.CTP3.nLacZ

The transfer vector for CTL503 was constructed by cloning the $TCFC_{d=25}$-E1BTATA promoter as a HindIII fragment upstream of the NTR gene in HindIII-digested pTX0374, so removing the CMV promoter from the latter. The new expression cassette was cloned into pPS1128 as a SpeI fragment to create pPS1128/$TCFC_{d=25}$-E1BTATA.

The transfer vector for Ad.CTP1-nLacZ was constructed by cloning the an expression cassette comprising of a nuclear-targeted LacZ gene fused to the mouse protamine polyadenylation signal as an XbaI fragment into XmaI/SpeI-digested and blunted pTX0374. The CTP1 promoter was cloned upstream of the nLacZ gene as a HindIII fragment The CTP1-nLacZ expression cassette was then cloned in a left-to-right orientation into pPS1128 as a blunted, SpeI/NotI fragment into SpeI, blunted pPS1128 to create pPS1128/CTP1-nLacZ.

To construct the transfer vector for Ad.CTP3-nLacZ, in a first step the CTP3 promoter was cloned as a blunted, SpeI/HindIII fragment into HindIII-digested and blunted pTX0374, replacing the CMV promoter with CTP3. This cloning regenerated the HindIII site. In a second step, the resulting plasmid was digested with HindIII/PacI and then blunted to release the NTR gene and the IVSII intron/polyadenylation signal. The nLacZ-poly(A) cassette (see details described for the construction of CTP1-nLacZ) was cloned downstream of CTP3 as a blunted XbaI fragment. Finally the complete expression cassette was cloned into pPS1128 in a left-to-right orientation as a blunted, SpeI/NotI fragment into the PmeI site of a pPS1128 derivative (pTX0398) in which the unique SpeI site is replaced by a PmeI site to create pTX0398/CTP3-nLacZ.

Viruses were rescued by homologous recombination of the above transfer vectors with pPS1160 in PerC6 cells as described above (Construction of replication defective adenoviruses expressing NTR)

X-Gal Staining of Cells for Histology

After washing cells with PBS, cells were fixed in 0.05% glutaraldehyde in PBS for 10 min at RT. Following further washing in PBS, cells were incubated cells the following solution and incubated at 37° C. X-gal solution: 400 µl 500 mM $K_4Fe(CN)_6$, 400 µl 500 mM $K_3Fe(CN)_6$, 100 µl 2 mM $MgCl_2$, 250 µl 40 mg/ml X-Gal in DMF and 8.85 ml PBS.

Quantitation of β-Galactosidase Expression

Expression of β-galactosidase was measured for quantitative graphical presentation by means of the Galacto-Light system (Tropix Inc, Applied Biosystems, Foster City, Calif., U.S.A.)

EXAMPLES

Example 1

A 5merTcf-SV40-Luciferase Construct is Specifically Activated in Tumour Cell Lines with Deregulated β-catenin Activity.

To evaluate the ability of β-catenin/Tcf binding elements to direct high-level gene expression specifically in cells with deregulated β-catenin activity we constructed a luciferase reporter plasmid containing an artificial promoter comprising of 5 Tcf sites upstream of the basal SV40 promoter. In HeLa cells (β-catenin not deregulated) the 5merTcf-SV40 was not more active than the SV40 promoter alone. In contrast, in cell lines with deregulated β-catenin the 5merTcf-SV40 promoter expressed at about 80% activity of the CMV enhancer/promoter (SW480 cells) and was even more active than CMV (HepG2). The induction ratios for the 5merTcf-SV40 were 18 (HepG2) and 44.2 (SW480). These data indicate that the Tcf sites are active only in the presence of nuclear β-catenin. In some experiments the activity of the 5merTcf-SV40 promoter in Hela cells was even lower than the activity of SV40 alone (data not shown). This is consistent with the fact that Tcf factors normally repress transcription e.g. by interacting with the transcriptional cofactor CBP (cAMP binding protein) if β-catenin is not present to create β-catenin/Tcf heterodimers.

Example 2

The Activity and Specificity of the 5merTcf-SV40 Artificial Promoter is Retained in a Replication Defective Adenovirus Vector.

To evaluate the utility of the 5merTcf-SV40 promoter to drive the high-level expression of a therapeutic gene selectively in tumours comprising of cells with deregulated β-catenin, for instance a tumour of colorectal origin, we constructed a replication defective Adenovirus vectors expressing the E. coli B nitroreductase gene (NTR) under the control of the 5merTcf-SV40 promoter. The NTR gene encodes an enzyme that can convert the prodrug CB1954 into a potent DNA cross-linking agent that can kill both dividing and non-dividing cells. Clones 1 (CTL501) and 13 contain the cassette in the indicated orientation (FIG. 2a). In CTL102, the CMV enhancer/promoter regulates NTR expression. CsCl-banded viruses were prepared and HeLa, HepG2 and SW480 cells were infected with the indicated mois (FIG. 2b). In this case the left-to-right orientation of clone 1 was found to offer slightly greater specificity of expression, as shown, and this became the standard orientation adopted (CTL501). As expected CTL102 showed NTR expression in all three cell lines independent of their β-catenin status. In contrast, CTL501 was highly active only in HepG2 and SW480 cells. Even at a 5× higher moi NTR expression was barely detectable in HeLa cells. Clone 13 whilst as active as CTL501 in HepG2 and SW480 cells also expressed in Hela although still at a relatively low level compared to the former.

Example 3

The Tcf-Responsive Adenovirus CTL501 Shows Anti-tumour Activity In Vivo.

Having established that CTL501 can express high levels of NTR in permissive cells in vitro we tested whether intratumoral injection of HepG2 xenografts with the virus resulted in the expression of sufficient enzyme to sensitise the tumours to CB1954 and cause measurable anti-tumour effects including tumour regression. In the experiment 4 out of 5 tumours underwent clear regression (FIG. 3). After 56 days two of the four responders could be categorised as complete regressions and two animals harboured a quiescent, very small tumour. Tumours injected with vehicle only and treated with CB1954 grew out as expected. Interestingly virus injection alone resulted in an apparent slowing of tumour growth. We attribute the variable response to the treatment to the inherent variability of the intratumoral injection technique.

Example 4

High Level Expression of NTR in CTL501-Injected SW480 Xenografts.

Having demonstrated that CTL501 is highly active in SW480 colorectal cancer cells in vitro we determined whether high level NTR expression could be obtained by intratumoral injection of subcutaneous SW480 xenografts in nude mice. Four tumours were injected with either CTL102 or with CTL501 and 48 hours later, following humane sacrifice, were excised, fixed, sectioned and immunostained for NTR expression. The results are summarised in FIG. 4. These provide further evidence that CTL501 expresses NTR at a level at least comparable to CTL102. We attribute the significant variation in the percentage of cells that are NTR positive to the inherent variability of the intratumoral injection technique.

Example 5

Systemic Administration of Adenovirus Followed by CB1954 Treatment: CTL501 is Much Less Toxic than CTL102 (CMV-NTR).

We show above that intratumoral injection of CTL501 results in high level NTR expression. Associated with this method of obtaining specific delivery of a therapeutic gene to tumour cells however is the danger of virus dissemination, in particular via the bloodstream to the liver. Based on the in vitro specificity data presented above we predicted that whereas intravenous injection of nude mice with CTL102 would result in high level expression of NTR in the liver and consequently significant toxicity of CB1954, injection of CTL501 would be relatively very well tolerated as this should result in very little or no liver expression of NTR. The results shown in FIG. 5 support this. Whereas a dose of 10E9 particles of CTL501+CB1954 treatment resulted in virtually no toxicity, a tenfold lower dose of CTL102 resulted in 100% mortality. We conclude that CTL501 expresses no, or an insignificant amount of, NTR in normal cells, in particular the liver.

Example 6

Construction of an Improved Tcf-Based Promoter that is Fully Inactive in Cells Lacking β-catenin Activity.

For some applications it would be desirable to increase the specificity of the 5merTcf-based artificial promoter further, for instance to control the replication of a therapeutic adenovirus. We therefore evaluated the combination of the 5merTcf element described above with the adenoviral (Ad5) E1B gene TATA box (5merTcf-E1BTATA-Luc (CTL502), FIG. 6a). As shown above, in transient transfections in HeLa and SW480 the 5merTcf-SV40 promoter is highly active in SW480, here comparable to CMV, but shows a background activity in HeLa cells due to the basal activity of the SV40 promoter. In contrast, the 5merTcf-E1BTATA-luc construct although less active in SW480 (60% activity of 5merTcf-SV40) was completely inactive in HeLa (not deregulated β-catenin). Expressed another way, replacement of the SV40 minimal promoter with the E1BTATA element resulted in an increase in inducibility in SW480 compared to HeLa from about 30–60 fold for 5merTcf-SV40 to about 600–2,000 fold for 5merTcf-E1BTATA i.e. a 20fold improvement.

Example 7

The Activity of the 5merTcf-SV40 and 5merTcf-E1BTATA Promoter Constructs is Dependent on the Relative Positioning of the Tcf Sites.

To determine whether changing the arrangement of the sites along the DNA helix influences the activity of 5merTcf-based promoter constructs we constructed "TcfA", "TcfB" and "TcfC" (FIG. 7) in combination with either the SV40 minimal promoter or the E1BTATA and compared their activity with the respective original 5mer Tcf-based promoters i.e. +SV40 or +E1BTATA. In transiently transfected SW480 cells, the highest level of reporter gene expression was obtained with the TcfC-E1BTATA promoter element (FIG. 8a). The lowest level of expression was obtained with the E1BTATA-TcfB combination which was about half as active as TcfC-E1BTATA. For the SV40 combinations less variation in expression was observed (FIG. 8b).

Furthermore in marked contrast to the result with E1BTATA, the TcfC-SV40 promoter was the least active and the TcfB-SV40 the most active. These results suggest that the optimum spacing of the Tcf sites is dependent on the basal promoter that is combined with the Tcf elements. Further evidence for a critical role in the spacing of Tcf sites in determining the level of expression in β-catenin deregulated cells is provided in FIG. 9. This shows the results of transient transfections of SW480 with Tcf-E1BTATA-luc constructs containing fewer than 5 Tcf sites (2, 3 and 4). Whilst there is a general increase in expression with an increasing number of sites, the results also show that by appropriate spacing of 3 sites a higher level of expression was obtained compared to an alternative arrangement of 4 sites.

None of the constructs described above exhibited an increased background expression level in Hela compared to the original 5merTcf-based promoters i.e. alteration of the spacing of the Tcf sites does not result in a loss of the exquisite specificity we have described above.

Example 8

The Activity of the TcfC-E1BTATA Promoter Element is Determined by the Distance Between the Tcf Binding Sites and the E1BTATA Box.

We also determined the effect on expression of changing the distance between the Tcf binding sites and the TATA box (FIG. 10). Four constructs based on the TcfC-E1BTATA were constructed and compared (FIG. 10a—and see the materials and methods section). As shown in FIG. 10b an inverse relationship was discovered between the Tcf-to-TATA separation and the level of luciferase expression in transfected SW480 cells. Although expression may be further improved by reducing the separation further it is likely that 25 bp is approaching the minimum separation. As below this the initiation complexes and Tcf/β-catenin would be expected to sterically hinder access to their respective binding sites. The new constructs tested here retained the specificity of the original 5merTcf-E1BTATA artificial promoter (data not shown).

Example 9

The Activity and Specificity of the 5merTcf-E1BTATA Promoter is also Retained in a Replication Defective Adenovirus.

To confirm that the 5merTcf-E1BTATA (CTL502) promoter also retains its activity and specificity in the context of adenovirus we infected HeLa and SW480 cells with CTL102, CTL501 and CTL502 and assayed NTR expression by ELISA (FIG. 11). As expected, CTL102 was highly active in both HeLa and SW480. Consistent with transient transfection studies shown above, both CTL501 and CTL502 were highly active in SW480 but only very weakly active in HeLa. Furthermore, CTL502 was apparently less active than CTL501 in HeLa. Whereas CTL501 expressed a clearly detectable level of NTR at high moi (1500 pfu/cell) this was not detected with CTL502. The combination of β-catenin/Tcf responsive elements with the adenoviral (Ad5) E1BTATA box thus provides an extremely high level of tumour selectivity likely to be suitable for the expression of genes encoding highly potent therapeutic agents which could significantly damage non-cancerous cells even at low levels.

Example 10

Intravenous Injection of CTL501 and CTL 102 into Normal Mice: Lack of Liver Expression with CTL501

We show above (Example 5) that systemic administration of CTL501 to normal mice (tail vein injection) followed by CB1954 treatment is very well tolerated. In contrast, injection of a tenfold lower dose of CTL102 (CMV.NTR)/CB1954 combined with CB1954 was lethal in all cases. We concluded from this result that the β-catenin/Tcf-responsive promoter driving the NTR gene in CTL501 is inactive or at most weakly active in normal mouse tissues infected by the virus, principally the liver. To provide direct evidence for this, mice were injected with CTL501 or CTL102 and liver expression determined by immunostaining 48 h post-injection. In FIG. 12 we show representative liver sections stained for NTR expression. Injection of CTL501 resulted in sporadic, low-level NTR expression whereas a 10 fold lower dose of CTL102 generated high level expression in a majority of cells. We interpret this result and that described in Example 5 to indicate that the β-catenin/Tcf-4 complex is either absent from or present at too low a level in the nuclei of normal mouse hepatocytes to activate the promoter. It is highly unlikely that these data reflect an inability of murine beta-catenin/Tcf-4 to activate the promoter as (i) the Wnt pathway is evolutionarily highly conserved from flies upwards and (ii) the promoter of at least one murine gene that is activated by Wnt signalling (cdx) contain Tcf binding sites that fit the consensus human Tcf-4 binding site that we have used to build the promoter (Lickert et al (2000) *Development* 127: 3805–3813).

Example 11

CTL501I/CB1954 Anti-tumour Efficacy in a Xenograft Model of Colorectal Cancer

We show above in Example 3 that i.t. injection of HepG2 (liver cancer) xenografts with a single dose of CTL501 strongly sensitised this β-catenin-deregulated tumour model to the prodrug CB1954, resulting in tumour regression in the majority of cases. We show here that CTL501/CB1954 therapy is highly effective in a xenograft model of β-catenin-deregulated colorectal cancer (SW480). Two size randomised groups of tumours were injected with $10^9$ and $10^{10}$ particles of CTL501 respectively and CB1954 administered to the host mice beginning 48 h later. So as to be able to compare the efficacy observed to that achievable when NTR was expressed from the CMV promoter, two additional tumour groups were injected with equivalent doses of CTL102. As shown in FIG. 13, CTL501 and CTL102 injection resulted in a similar level of anti-tumour efficacy. Non-virus injected control tumours (vehicle injected+systemic CB1954 treatment) grew strongly.

Example 12

CTL503/CB1954 Anti-tumour Efficacy in a Xenograft Model of Colorectal Cancer

We show above (Examples 6–8) that it is possible to build a β-catenin/Tcf-4 responsive promoter with an increased dependence on β-catenin/Tcf-4 (and therefore improved specificity for tumours with deregulated β-catenin) by substitution of the SV40 minimal promoter fragment with the Ad5 E1B TATA and by altering the spacing between the Tcf binding sites and between the E1B TATA and promoter-proximal Tcf-4 binding site. A recombinant virus ("CTL503") was constructed containing this modified promoter driving NTR to determine whether the high level expression in permissive cells observed using transient transfection experiments would be retained in the context of an adenovirus backbone. In FIG. 14 we show that i.t. injection of SW480 xenografts with CTL503 and subsequent CB1954 administration resulted in an anti-tumour response of a similar magnitude to that resulting from CTL102+CB1954 treatment. These in vivo efficacy data thus provide strong evidence that the improved tumour specificity of CTP3, detected by transient transfection experiments was gained with retention of a high level of activity in tumour cells with deregulated β-catenin/Tcf-4.

Example 13

The β-catenin/Tcf-Dependent Promoters Express at Very Low Levels in Cultured Primary Human Hepatocytes, Dermal Fibroblasts and Endothelial Cells We show above that the claimed promoters express at very low levels in tumour cell lines that retain normal β-catenin regulation. From this we infer that these promoters will be inactive/weakly expressed in normal human cells, i.e. we used the tumour cells to model normal cells. To provide direct evidence for this we determined the activity of two of the promoters in a panel of cultured primary human cells (hepatocytes, endothelial cells and dermal fibroblasts). To facilitate these and subsequent studies involving cultured primary human tissue (see Examples 15 and 16 below) we constructed recombinant adenoviruses expressing beta-galactosidase under the control of two of the claimed promoters, "Ad.CTP1-nLacZ" and "Ad.CTP3-nLacZ" (in the interest of clarity we now use a systematic nomenclature for the promoters: the original promoter present in CTL501 is renamed as "CTP1"; the optimised promoter present in CTL503 is renamed as "CTP3").

FIG. 15 shows that the CMV promoter expressed strongly in all three cell types tested whereas CTP1 and CTP3 directed very low levels of beta-galactosidase expression in these cells. All three promoters were however strongly active in SW480 colon cancer cells (FIG. 15d)

Example 14

CTP1 and CTP3 Direct Very Low Levels of Transgene Expression During Growth of an E1-Deleted Adenovirus in the 293 and PerC6 Helper Cell Lines Attempts to grow E1-deleted viruses encoding cytotoxic genes driven by promoters that are active in E1-expressing Ad helper cells are generally unsuccessful as expression of the toxic gene product prevents the cells from supporting efficient virus growth.

To determine the level of expression of the CTP1 and CTP3 promoters during virus production we infected 293 and PerC6 cells with Ad.CMV-nLacZ, Ad.CTP1-nLacZ and Ad.CTP3-nLacZ viruses and determined the level of LacZ expression 30 h post-infection.

In FIG. 16 we show that LacZ expression driven by CTP1 and CTP3 was significantly lower than that driven by the CMV promoter in both Ad helper lines. However, as observed in all other non-permissive cell lines, CTP3 was clearly less active than CTP1 (approximately 10 fold). Both promoters were approximately 3 fold more active in PerC6 than in 293 cells. These data suggest that both cell lines but in particular 293 cells would support the efficient replication of first generation Adenovirus vectors encoding a toxic transgene under the control of the CTP3 promoter.

Example 15

CTP1 and CTP3 Promoters are Highly Active in Freshly Excised Metastatic Colorectal Cancer Tissue but Inactive in Associated Liver Tissue Established tumour cell lines are useful model systems to study gene expression patterns in cancer. These lines are however cloned from primary cancers, which are polyclonal populations of genetically diverse and genetically unstable cells. They have also generally been continuously cultured for long periods of time, providing further scope for the selection of cells that are well adapted to ex vivo culture but not very representative of the cancer from which they were derived. For these reasons we determined the activity of CTP1 and CTP3 in freshly explanted samples of primary and secondary colorectal cancer. Samples were prepared and infected with Ad.CMV-nLacZ, Ad.CTP1-nLacZ and Ad.CTP3-nLacZ viruses and analysed for nuclear beta-galactosidase expression as described in the Materials and methods section. Ad.CMV-nLacZ was used to determine the viability of each sample and susceptibility to adenovirus infection and to allow a comparison of the relative activities of CMV and CTP1/3 promoters. FIG. 17 shows the results obtained with a secondary cancer isolated from the liver. For each virus treatment, tumour with attached liver margin was incubated in the virus suspension. As observed with all other tumour specimens, the tissue was free of endogenous beta-galactosidase activity (mock-infected samples not stained by X-Gal). Incubation with Ad.CMV-nLacZ resulted in strong staining of both tumour and attached liver. A striking demonstration of tumour specificity was provided by infection of equivalent samples with Ad.CTP1-nLacZ and Ad.CTP3-nLacZ viruses: in both cases exposure of liver and tumour tissue resulted in a level of expression equivalent to CMV but restricted to tumour tissue. To date, all 5 colorectal metastases examined were permissive for high-level CTP1 and CTP3 expression. Of 10 primaries, 3 were found to be weakly or non-permissive for promoter activity. Of note, the primary tumours that gave rise to the secondaries were permissive in each case.

Example 16

Figure 18:
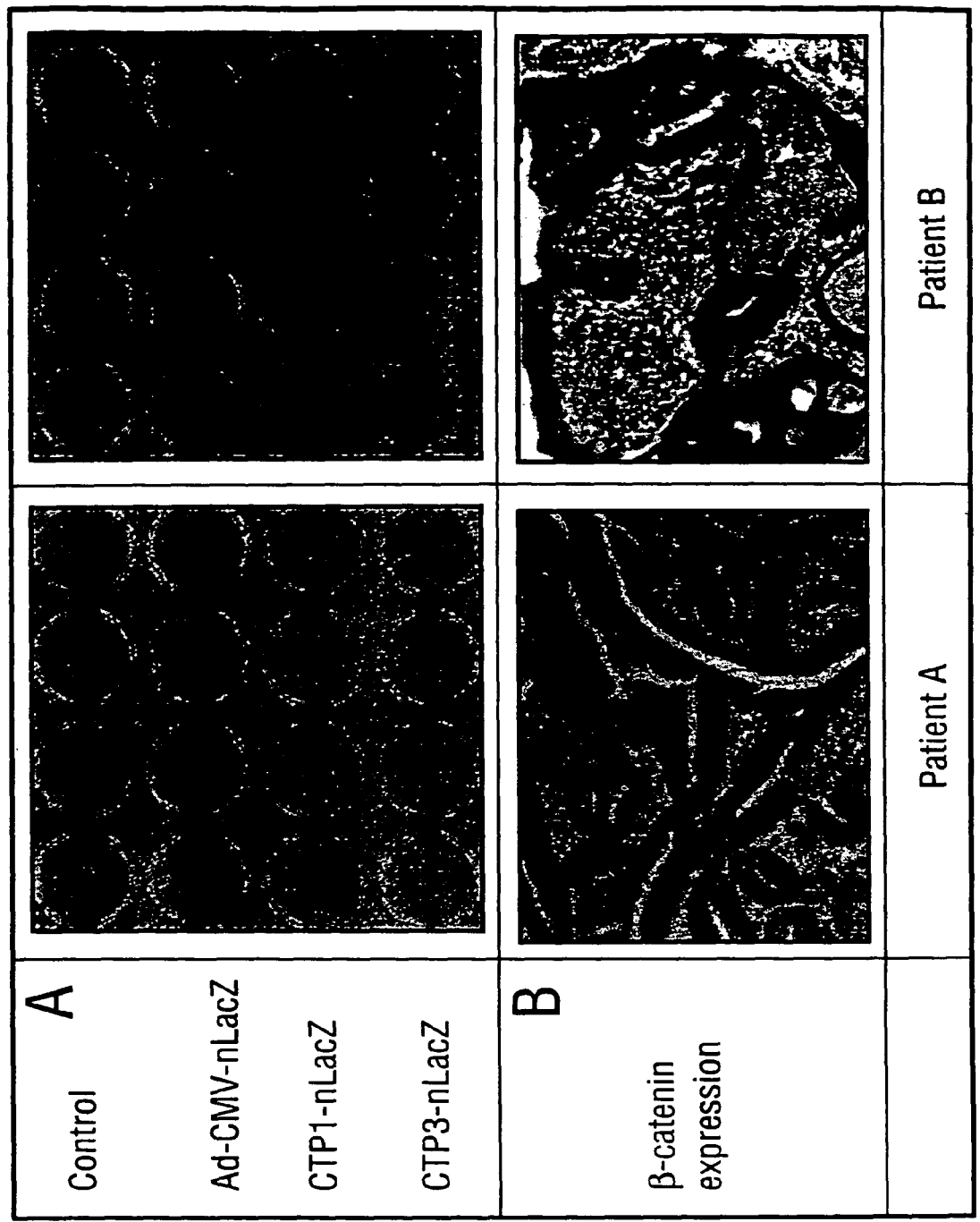

High-level CTP-Mediated Expression Correlates with High Level, Non-membranous Expression of Beta-catenin In Example 15 we demonstrate that CTP1 and CTP3 can provide high-level gene expression selectively in secondary colorectal cancer tissue despite the simultaneous introduction of the transgene into neighbouring healthy liver tissue. Whilst to date the promoters were active in all secondary CRC deposits, low-level or undetectable expression was observed in 3 of 10 primaries. Analysis of these non-permissive tumours for beta-catenin revealed a correlation between the overall level and sub-cellular distribution of the protein. FIG. 18 shows the results for representative permissive and non-permissive tumour samples. Tumour A (non-permissive) is relatively well-differentiated with beta-catenin staining restricted largely to the cell periphery, consistent with this being associated with E-cadherin. Tumour B (permissive) in contrast is poorly differentiated with a significantly higher level of cytoplasmic/nuclear beta-catenin staining. This finding provides further evidence for a dependence of the CTP promoters on beta-catenin deregulation. It conflicts with the simple model of colon carcinogenesis in which beta-catenin deregulation resulting in constitutive activation of genes responsive to beta-catenin/Tcf is the initiating event. A practical application of this finding is that it may provide the basis for pre-selection of patients possessing tumours that are permissive for the CTP promoters and thus potentially treatable by a gene therapy approach in which a therapeutic gene is under the control of a CTP promoter.

All references cited herein are hereby incorporated by reference in their entireties.

What is claimed is:

1. A nucleic acid construct comprising: a T-cell factor (TCF) response element comprising:
    at least one TCF binding element having the sequence CTTTGNN wherein N is A or T;
    an operably linked promoter; and
    an expressible gene selected from the group consisting of:
        a gene encoding a toxin, a gene encoding a prodrug-activating enzyme, a gene encoding an immunomodulatory agent, a tumor-suppressor gene, and an apoptotic gene, wherein the expressible gene is operably linked to both the TCF binding element and the promoter, which enables inducible expression of the gene.

2. The nucleic acid construct of claim 1, wherein the expressible gene encodes a toxin or prodrug-activating enzyme.

3. The nucleic acid construct of claim 2, wherein the expressible gene encodes a nitroreductase capable of activating CB1954.

4. The nucleic acid construct of claim 1, wherein the promoter is selected from the group consisting of an SV40 promoter, an E1B promoter, and a c-Fos promoter.

5. The nucleic acid construct of claim 4, wherein the promoter is the E1B promoter.

6. A nucleic acid construct comprising: 1) a TCF response element comprising: at least 5 TCF binding elements having the sequence CTTTGNN, wherein N is A or T; and an operably linked promoter; and 2) an expressible gene selected from the group consisting of: a gene encoding a toxin, a gene encoding a prodrug-activating enzyme, a gene encoding an immunomodulatory agent, a tumor-suppressor gene, and an apoptotic gene.

7. The nucleic acid construct of claim 6 wherein the TCF response element comprises between 5 and 10 TCF binding elements.

8. The nucleic acid construct of claim 7 wherein the TCF response element comprises 5 TCF binding elements.

9. A nucleic acid construct comprising: 1) a TCF response element comprising: at least two TCF binding elements having the sequence CTTTGNN, wherein N is A or T; and an operably linked promoter, and 2) an expressible gene selected from the group consisting of: a gene encoding a toxin, a gene encoding a prodrug-activating enzyme, a gene encoding an immunomodulatory agent, a tumor-suppressor gene, and an apoptotic gene, wherein the expressible gene is operably linked to the TCF response element which enables inducible expression of the gene, and wherein the TCF binding elements are separated from each other by between 3 and 20 nucleotides.

10. The nucleic acid construct of claim 9 wherein the TCF binding elements are separated from each other by between 3 and 12 nucleotides.

11. The nucleic acid construct of claim 10 wherein the TCF binding elements are separated from each other by between 10 and 12 nucleotides.

12. The nucleic acid construct of claim 9 wherein the TCF binding elements are separated from each other by 3 or 4 nucleotides and wherein the promoter comprises a TATA box, and the TCF binding element closest to the promoter is 25 nucleotides from the TATA box of the promoter.

13. A nucleic acid construct comprising: 1) a TCF response element comprising: at least one TCF binding element having the sequence CTTTGNN, wherein N is A or T; and an operably linked promoter comprising a TATA box; and 2) an expressible gene selected from the group consisting of: a gene encoding a toxin, a gene encoding a prodrug-activating enzyme, a gene encoding an immunomodulatory agent, a tumor-suppressor gene, and an apoptotic gene, wherein the expressible gene is operably linked to the TCF response element which enables inducible expression of the gene, and wherein the TCF binding element closest to the promoter is between 140 and 10 nucleotides from the TATA box of the promoter.

14. The nucleic acid construct of claim 13 wherein the promoter contains a TATA box, and the TCF binding element closest to the promoter is between 100 and 10 nucleotides from the TATA box of the promoter.

15. The nucleic acid construct of claim 14 wherein the promoter contains a TATA box, and the TCF binding element closest to the promoter is between 50 and 10 nucleotides from the TATA box of the promoter.

16. The nucleic acid construct of claim 15 wherein the promoter contains a TATA box, and the TCF binding element closest to the promoter is between 30 and 15 nucleotides from the TATA box of the promoter.

17. The nucleic acid construct of any one of claims 1, 6, 9, or 13, wherein the TCF binding element or elements have the nucleotide sequence CTTTGAT.

18. A vector comprising the nucleic acid construct of any one of claims 1, 6, 9, or 13.

19. An isolated host cell transfected with the vector of claim 18.

20. A composition comprising the nucleic acid construct of any of claims 1, 6, 9 or 13 and a pharmaceutically acceptable excipient.

21. A composition comprising the vector of claim 18.

22. A composition comprising the host cell of claim 19 and a pharmaceutically acceptable excipient.

* * * * *